US012630724B2

(12) United States Patent
Oowada et al.

(10) Patent No.: US 12,630,724 B2
(45) Date of Patent: May 19, 2026

(54) PATTERN FORMING METHOD AND PLASMA PROCESSING METHOD

(71) Applicants: Tokyo Electron Limited, Tokyo (JP); TOKYO INSTITUTE OF TECHNOLOGY, Tokyo (JP)

(72) Inventors: Shin Oowada, Tokyo (JP); Tatsuya Yamaguchi, Yamanashi (JP); Ryuichi Asako, Yamanashi (JP); Takanori Fukushima, Tokyo (JP); Yoshiaki Shoji, Tokyo (JP); Takashi Kajitani, Tokyo (JP); Hibiki Ogiwara, Tokyo (JP)

(73) Assignees: Tokyo Electron Limited, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 208 days.

(21) Appl. No.: 18/574,204

(22) PCT Filed: Jun. 27, 2022

(86) PCT No.: PCT/JP2022/025607
§ 371 (c)(1),
(2) Date: Dec. 26, 2023

(87) PCT Pub. No.: WO2023/282114
PCT Pub. Date: Jan. 12, 2023

(65) Prior Publication Data
US 2024/0318014 A1 Sep. 26, 2024

(30) Foreign Application Priority Data
Jul. 9, 2021 (JP) ................................. 2021-114353

(51) Int. Cl.
| *C09D 7/63* | (2018.01) |
| *C07C 43/21* | (2006.01) |
| *C07F 7/18* | (2006.01) |

(52) U.S. Cl.
CPC ................ *C09D 7/63* (2018.01); *C07C 43/21* (2013.01); *C07F 7/1804* (2013.01); *C07C 2603/90* (2017.05)

(58) Field of Classification Search
CPC ......... H01L 21/31138; H01L 21/31116; H01L 21/30156
See application file for complete search history.

(56) References Cited

U.S. PATENT DOCUMENTS

| 2012/0229709 A1* | 9/2012 | Heald | B81C 1/00269 348/E5.133 |
| 2017/0279058 A1* | 9/2017 | Fukushima | H10K 10/471 |
| 2021/0320185 A1* | 10/2021 | Lee | H10D 64/679 |

FOREIGN PATENT DOCUMENTS

| JP | 2014-126623 | 7/2014 |
| JP | 2014-241374 | 12/2014 |

(Continued)

OTHER PUBLICATIONS

Ishiwari Fumitaka et al: "Terminal Functionalization with a Triptycene Motif That Dramatically Changes the Structural and Physical Properties of an Amorphous Polymer", Langmuir, vol. 140, No. 41, Oct. 3, 2018. Oct. 3, 2018), pp. 13497-13502, XP093105554, DOI: 10.1021/jacs.8b09242.

*Primary Examiner* — Thomas T Pham
(74) *Attorney, Agent, or Firm* — IPUSA, PLLC

(57) ABSTRACT
A pattern forming method includes forming a pattern film on a substrate. The pattern film includes a triptycene derivative having a triptycene skeleton. The triptycene skeleton includes a first plane in which position 1, position 8, and position 13 of the triptycene skeleton are arranged, and a (Continued)

second plane in which position 4, position 5, and position 16 of the triptycene skeleton are arranged. The triptycene derivative includes a first side chain on a one plane side, the one plane side being on a side of one plane from among the first plane and the second plane, and a second side chain on another plane side or on the one plane side, the another plane side being on a side of another plane from among the first plane and the second plane. The second side chain is different from the first side chain in an etching selectivity ratio.

18 Claims, 28 Drawing Sheets

(56) References Cited

FOREIGN PATENT DOCUMENTS

| JP | 2017-505709 | 2/2017 |
| JP | 6219314 | 10/2017 |
| JP | 6272242 | 1/2018 |
| JP | 6793946 | 12/2020 |

* cited by examiner

COMPOUND OF
TRIPLE CHAIN ×
TRIPLE CHAIN

IN-PLANE DIRECTION:
NO DIFFRACTION

OUT-OF-PLANE DIRECTION:
1D LAMELLAR PHASE-SEPARATED
STRUCTURE

TEG-Trip-C12

*SCHEMATIC VIEW
OF MEASUREMENT SETUP

HORIZONTAL
INCIDENCE $q_z$ $q_{xy}$ $q_{xy}$

Pre-patterned
substrate

X-ray

*SCHEMATIC VIEW
OF ASSEMBLY STRUCTURE

~6.2 nm

Perpendicular
Orientation

Substrate 2.09 nm
($d_{003}$)

| | | | |
|---|---|---|---|
| CF–BASED 50 sec | 1 | 1.2 | 1.6 |
| OXYGEN–BASED 5 sec | 1 | 7.4 | 10.3 |

PATTERN FORMING METHOD AND PLASMA PROCESSING METHOD

TECHNICAL FIELD

The present disclosure relates to pattern forming methods and plasma processing methods.

BACKGROUND ART

Patent Literature 1 discloses a pattern forming method using a resist material including a base resin increased in alkali solubility by the action of acid, and a polymer additive including recurring units derived from styrene having an ester group bonded to a $CF_3$—$C(OR^2)$—$R^3$ group.

Patent Literature 2 discloses a pattern forming method of depositing a polymer material having a first segment and a second segment in a recessed portion of a guide having a pattern including projections and recesses, and microphase-separating the polymer material. This technique forms a self-assembled pattern including a cylindrical first polymer portion including the first segment and a second polymer portion including the second segment that encloses a lateral portion of the first polymer portion, and selectively removes the first polymer portion.

Patent Literature 3 discloses a technique of applying a directed self-assembly (DSA) composition including a block copolymer (BCP) to a substrate, and forming a pattern. In this technique, the BCP includes at least two blocks and is selected to have a high interaction parameter (Chi). The BCP forms vertical lamellae through simple thermal annealing on a neutralized substrate, without a top coat.

CITATION LIST

Patent Literature

Patent Literature 1: Japanese Laid-Open Patent Publication No. 2014-126623
Patent Literature 2: Japanese Laid-Open Patent Publication No. 2014-241374
Patent Literature 3: PCT Japanese Translation Patent Publication No. 2017-505709

SUMMARY OF INVENTION

Problem to be Solved by Invention

The present disclosure provides a pattern forming method that can form a fine pattern structure having etching resistance.

Means for Solving Problem

A pattern forming method according to one aspect of the present disclosure includes forming a pattern film on a substrate. The pattern film includes a triptycene derivative having a triptycene skeleton. The triptycene skeleton includes a first plane in which position 1, position 8, and position 13 of the triptycene skeleton are arranged, and a second plane in which position 4, position 5, and position 16 of the triptycene skeleton are arranged. The triptycene derivative includes a first side chain on a one plane side, the one plane side being on a side of one plane from among the first plane and the second plane, and a second side chain on another plane side or on the one plane side, the another plane side being on a side of another plane from among the first plane and the second plane. The second side chain is different from the first side chain in an etching selectivity ratio.

Advantageous Effects of Invention

According to one aspect of the present disclosure, it is possible to form a fine pattern structure having etching resistance.

BRIEF DESCRIPTION OF DRAWINGS

FIG. 5 is a view illustrating side chains of a triptycene skeleton.

FIG. 6 is a diagram illustrating a chemical structure of one example of a triptycene derivative having a structure including a triptycene skeleton, and a first side chain and a second side chain that are bonded to the triptycene skeleton in order and in series.

FIG. 9 is a diagram illustrating a chemical structure of one example of a triptycene derivative having a structure including a first side chain and a second side chain extending from the triptycene skeleton in opposite directions.

FIG. 12 is a diagram illustrating chemical structures of specific examples of the triptycene derivative represented by the general formula of FIG. 7.

FIG. 25 is a table illustrating the etching resistance for the side chains of the triptycene derivative.

DESCRIPTION OF EMBODIMENTS

Figure 1:
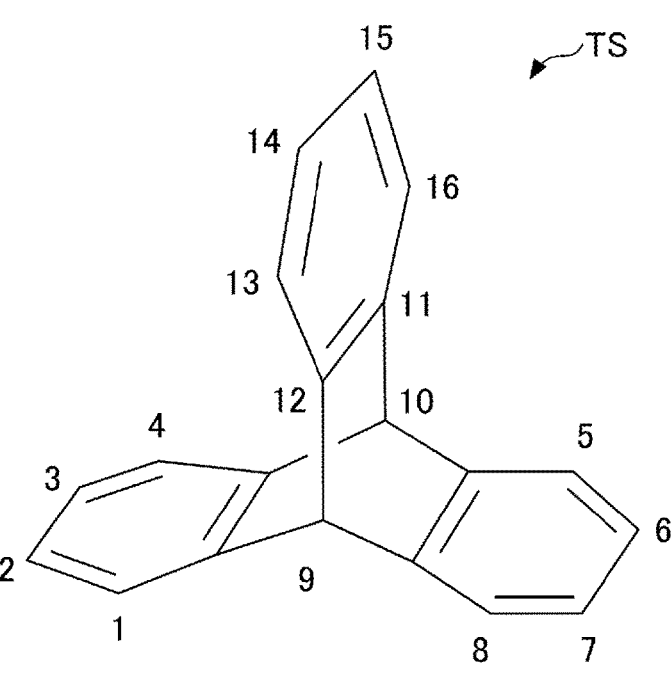
FIG. 1 is a diagram illustrating a chemical structure of triptycene.

Hereinafter, embodiments of the present disclosure will be described with reference to the drawings. Note that, common parts in the drawings are designated by the same or corresponding symbols, and description thereof may be omitted.

Figure 2:
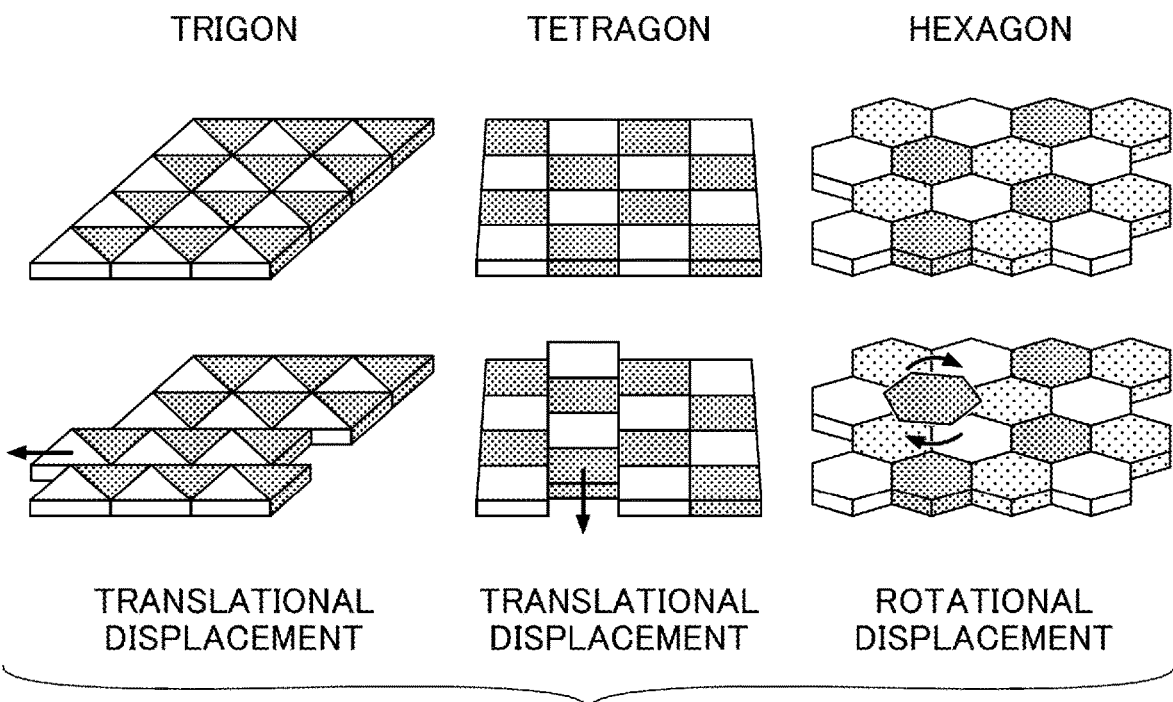
FIG. 2 is a schematic view illustrating assembly structures of molecules in existing pattern films.
Figure 3:
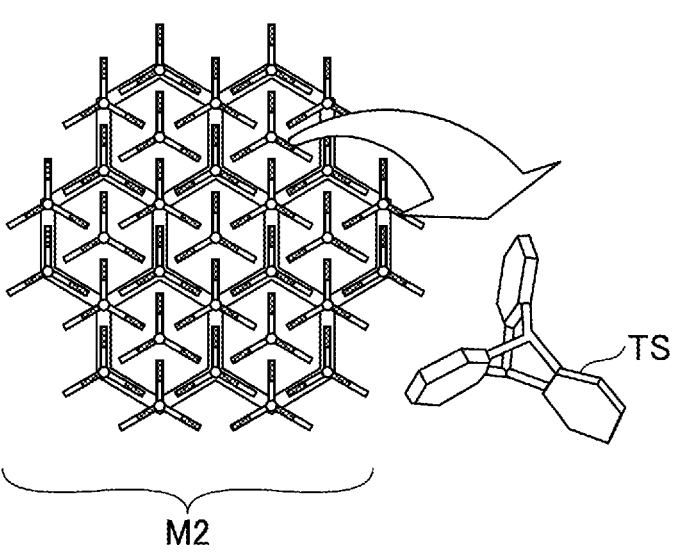
FIG. 3 is a view illustrating a two-dimensional assembly structure of triptycene.
Figure 4:
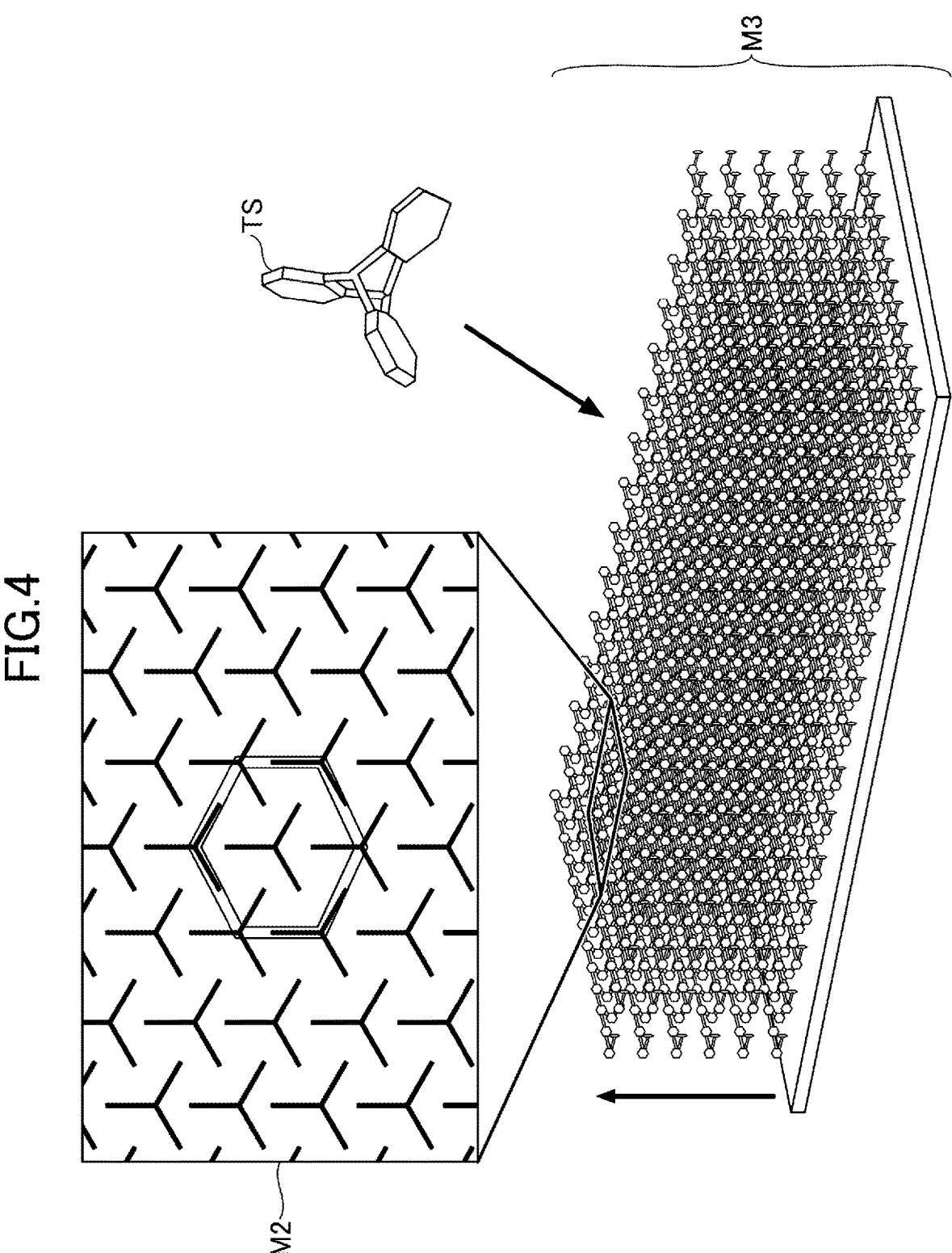
FIG. 4 is a view illustrating a three-dimensional assembly structure of triptycene.

FIG. 1 is a diagram illustrating a chemical structure of triptycene. FIG. 2 illustrates assembly structures of molecules in existing pattern films. FIG. 3 is a view illustrating a two-dimensional assembly structure of triptycene. FIG. 4 is a view illustrating a three-dimensional assembly structure of triptycene.

In the pattern forming method according to the present disclosure, a pattern film is formed on a substrate.

No particular limitation is imposed on the substrate. It is possible to use a substrate obtained by processing a wafer formed of single-crystal silicon (Si) through a semiconductor device production process. Also, the substrate may be a pattern substrate including silicon and an insulating layer on the silicon, such as a silicon oxide film (silicon oxide) or the like. Note that, the substrate is not limited to a wafer, and a glass substrate and the like for production of a flat panel display can also be used.

Examples of the pattern film include, but are not limited to, curable films for semiconductor elements, such as interlayer insulating films, spacers, protective films, colored pattern films for color filters, and the like. The thickness of the pattern film is, for example, from 0.1 through 10 μm, preferably from 0.1 through 5 μm, and more preferably from 0.1 through 3 μm.

Examples of the production method of the pattern film include, but are not limited to, various film forming methods such as vapor deposition, chemical vapor deposition (CVD), sputtering, spin coating, and the like. Note that, the CVD includes thermal CVD, plasma CVD, light CVD, and the like.

The pattern film includes the triptycene derivative having the triptycene skeleton. As illustrated in FIG. 1, triptycene is an aromatic hydrocarbon having a D, symmetric structure in which three benzene rings are disposed in the form of a propeller having three blades. In the present disclosure, position numbers of triptycene are indicated as position 1 to position 16 in accordance with the nomenclature of CAS (FIG. 1).

Note that, the triptycene skeleton in the present disclosure corresponds to triptycene TS as illustrated in FIG. 1. Also, in the present disclosure, triptycene (hereinafter may be referred to as a triptycene skeleton) is such that an imaginary plane in which position 1, position 8, and position 13 of the triptycene skeleton are arranged is defined as a first plane, and an imaginary plane in which position 4, position 5, and position 16 of the triptycene skeleton are arranged is defined as a second plane (see FIG. 1).

Here, properties of the triptycene will be described. In pattern films using existing polymer compounds, displacement tends to occur in an assembly structure M1 of molecules forming the pattern film. For example, a molecule having a trigonal chemical structure and a molecule having a tetragonal chemical structure tend to cause displacement in a translational direction. Also, a molecule having a hexagonal chemical structure tends to cause displacement in a rotational direction (see FIG. 2).

Meanwhile, because triptycene has a chemical structure in the form of a threefold symmetric propeller, displacement of a two-dimensional assembly structure M2 of the triptycene TS, which is disposed in a nested form, is suppressed both in the translational direction and in the rotational direction (see FIG. 3).

Also, a three-dimensional assembly structure M3 of the triptycene TS is an assembly structure in which the two-dimensional assembly structure M2 is stacked in a height direction or in a width direction. The three-dimensional assembly structure M3 of the triptycene TS can form a stack that is self-assembled in a height direction or in a width direction by being stacked while maintaining the orientation of the nested form of the two-dimensional assembly structure M2 of the triptycene TS.

The three-dimensional assembly structure M3 of the triptycene TS as described above forms a lamellar structure (a stack of thin-layered or plate-shaped structures) and forms a dense nanophase-separated structure as an assembly of organic molecules. This nanophase-separated structure can be strictly defined in terms of a size and a geometrical structure at a one-molecule level of the triptycene derivative (FIG. 4).

The pattern forming method of the present disclosure forms a pattern film including the triptycene derivative having the triptycene (triptycene skeleton) TS as described above. Note that, the triptycene derivative can be selected from the triptycene derivatives reported by one of the inventors of the present disclosure in Japanese Patent No. 6219314, Japanese Patent No. 6272242, Japanese Patent No. 6793946, and the like.

Of these triptycene derivatives, the present disclosure uses the triptycene derivative including: a first side chain on a one plane side, the one plane side being on a side of one plane from among the first plane and the second plane; and a second side chain on another plane side or on the one plane side, the another plane side being on a side of another plane from among the first plane and the second plane. In the triptycene derivative used, the first side chain and the second side chain are different from each other in an etching selectivity ratio.

Figure 5:
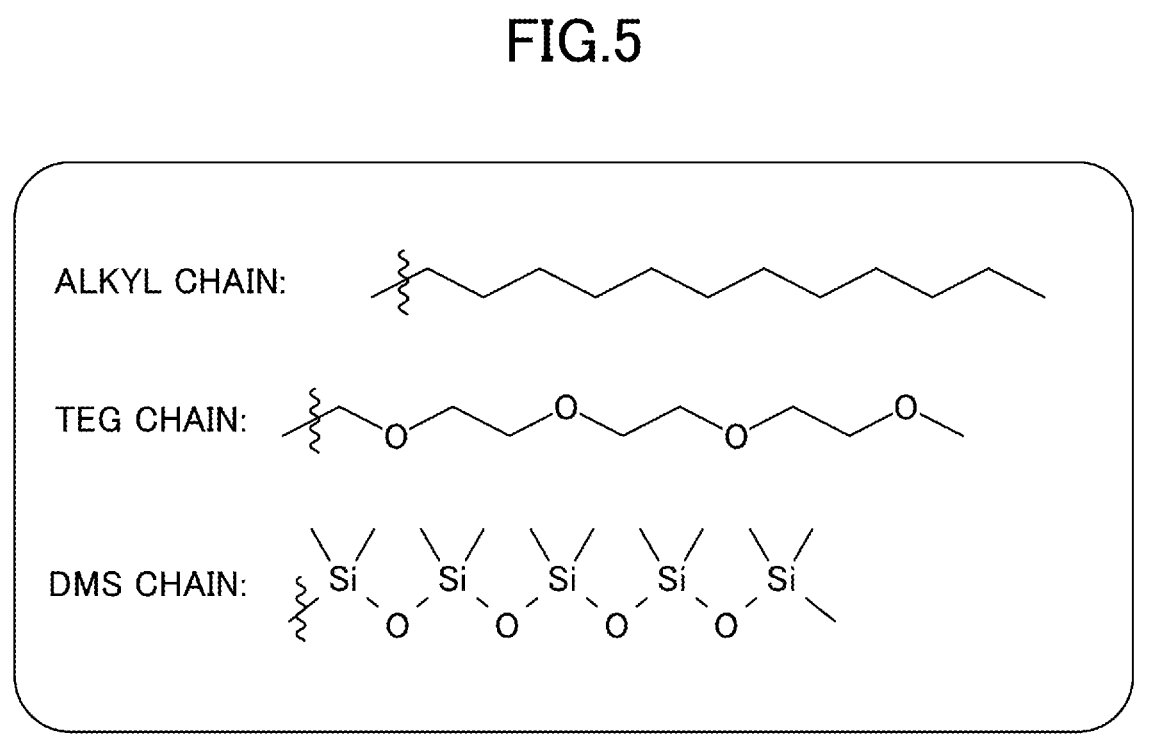

Here, examples of the first side chain and the second side chain include, but are not limited to: alkyl chains; a tetra-ethylene glycol chain (hereinafter referred to as a TEG chain); organic-composition side chains such as aryl chains and the like; inorganic-composition side chains of siloxane compounds and the like, including a dimethylsiloxane chain (hereinafter referred to as a DMS chain) and the like. Of these, the alkyl chain, the TEG chain, and the DMS chain are illustrated in FIG. 5. Note that, the side chain may be one forming an alkoxy chain that is bonded to the triptycene skeleton via oxygen.

Also, when the first side chain or the second side chain has an organic composition, the end of the first side chain or the second side chain having the organic composition is preferably hydroxy-terminated. Here, being hydroxy-terminated indicates a state in which the carbon atom at the end of the side chain having the organic composition is bonded to and terminated with a hydroxy group (OH group). For example, this corresponds to the side chains that are the TEG chains terminated with the OH group, as expressed by chemical formulae (3-1) to (3-4) in FIG. 12 described below.

The combination of the first side chain and the second side chain that are different from each other in an etching selectivity ratio is a given combination and may be determined in accordance with conditions for forming the pattern film. For example, when the alkyl chain or the TEG chain is used as the first side chain and the DMS chain is used as the second side chain in the below-described etching treatment, the first side chain is readily etched and the second side chain is not readily etched. In the present disclosure, the first side chain and the second side chain may be selected in consideration of such etchability.

In the present disclosure, the case in which the first side chain is included on the one plane side, which is the side of the one plane from among the first plane and the second plane, and the second side chain is included on the one plane side, which is the side of the one plane from among the first plane and the second plane, is specifically a case in which the first side chain is bonded to the triptycene skeleton at the one plane of the first plane and the second plane and the second side chain is further bonded to the end of the first side chain. That is, the first side chain and the second side chain are bonded in series in order of from the first side chain to the second side chain, and extend in the same direction.

In this way, no particular limitation is imposed on the triptycene derivative having the structure including the triptycene skeleton, and the first side chain and the second side chain that are bonded to the triptycene skeleton in order and in series. For example, as the triptycene derivative, it is possible to use a triptycene derivative in which the alkyl chain is bonded via oxygen (alkoxy group) to the first plane or the second plane of the triptycene skeleton, and the TEG chain is bonded to the end of the alkyl chain in series (see FIG. 6).

Figure 7:
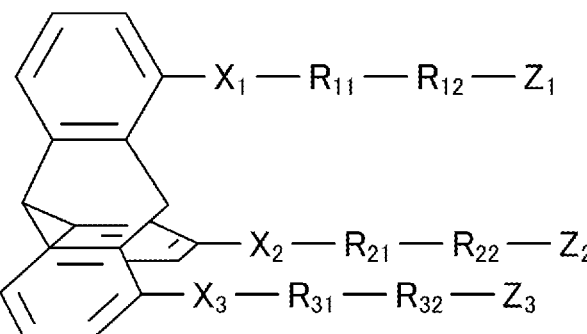
FIG. 7 is a diagram illustrating a general formula of a triptycene derivative having a structure including a triptycene skeleton, and a first side chain and a second side chain that are bonded to the triptycene skeleton in order and in series.

Note that, the triptycene derivative having the structure including the triptycene skeleton, and the first side chain and the second side chain that are bonded to the triptycene skeleton in order and in series is represented by the general formula in FIG. 7. In the general formula of FIG. 7, $R_{11}$, $R_{21}$, and $R_{31}$ correspond to the first side chain, and $R_{12}$, $R_{22}$, and $R_{32}$ correspond to the second side chain.

In the formula of FIG. 7, $R_1$, $R_{21}$, and $R_{31}$ are the same group, and represent a saturated or unsaturated divalent hydrocarbon group having from 5 through 30 carbon atoms. This hydrocarbon group may have one substituent or two or more substituents. Also, one carbon atom or two or more carbon atoms in the hydrocarbon group may be substituted with an oxygen atom, a sulfur atom, a silicon atom, or —NR7- (where R7 represents a hydrogen atom, an alkyl group having from 1 through 10 carbon atoms, or an aryl group having from 6 through 30 carbon atoms).

Also, in the formula of FIG. 7, $R_{12}$, $R_{22}$, and $R_{32}$ are the same group and are groups different from $R_{11}$, $R_{21}$, and $R_{31}$, and represent a saturated or unsaturated divalent hydrocarbon group having from 5 through 30 carbon atoms. This hydrocarbon group may have one substituent or two or more substituents. Also, one carbon atom or two or more carbon atoms in the hydrocarbon group may be substituted with an oxygen atom, a sulfur atom, a silicon atom, or —NR8- (where R8 represents a hydrogen atom, an alkyl group having from 1 through 10 carbon atoms, or an aryl group having from 6 through 30 carbon atoms).

Note that, in the formula of FIG. 7, $X_1$, $X_2$, and $X_1$ are the same group, and are a linking group (or a linker group) formed of a divalent atomic group including: from 1 through 5 atoms selected from the group consisting of a nitrogen atom, an oxygen atom, a sulfur atom, a carbon atom, and a silicon atom; and a hydrogen atom.

Also, in the formula of FIG. 7, $Z_1$, $Z_2$, and $Z_3$ are the same group, and are an end group (or a terminal group) formed of a hydrogen atom or formed of a monovalent atomic group including: from 1 through 15 atoms selected from the group consisting of a nitrogen atom, an oxygen atom, a sulfur atom, a carbon atom, a phosphorus atom, a halogen atom, and a silicon atom; and a hydrogen atom.

Figure 6:
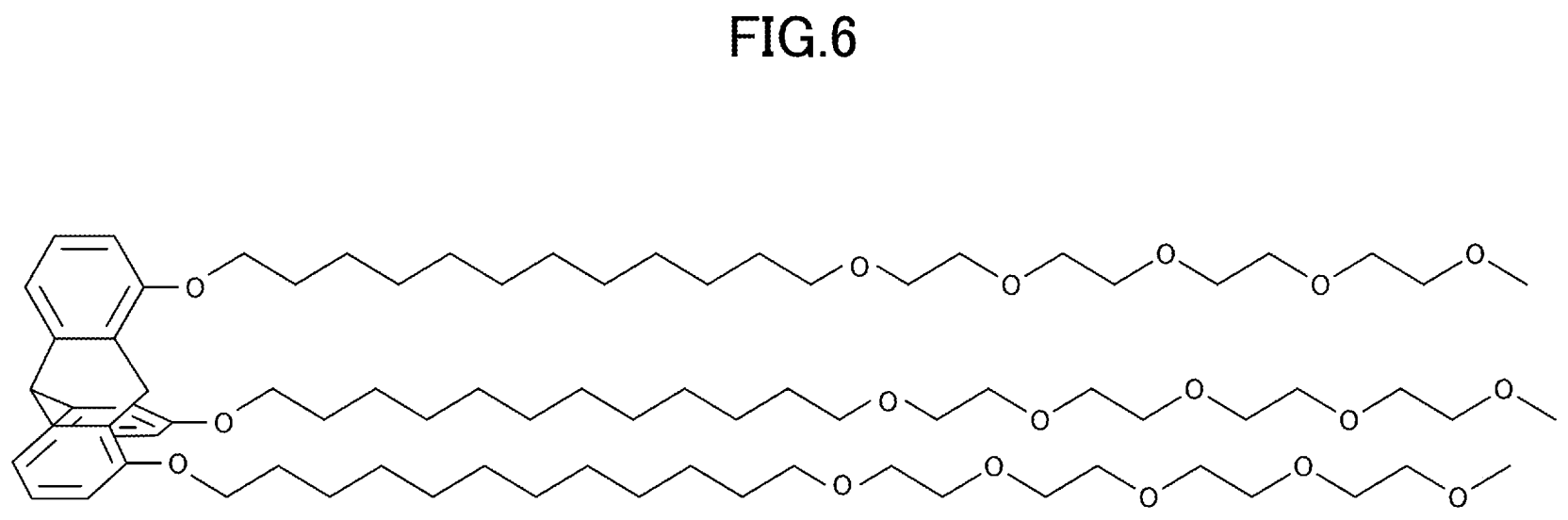
Figure 8:
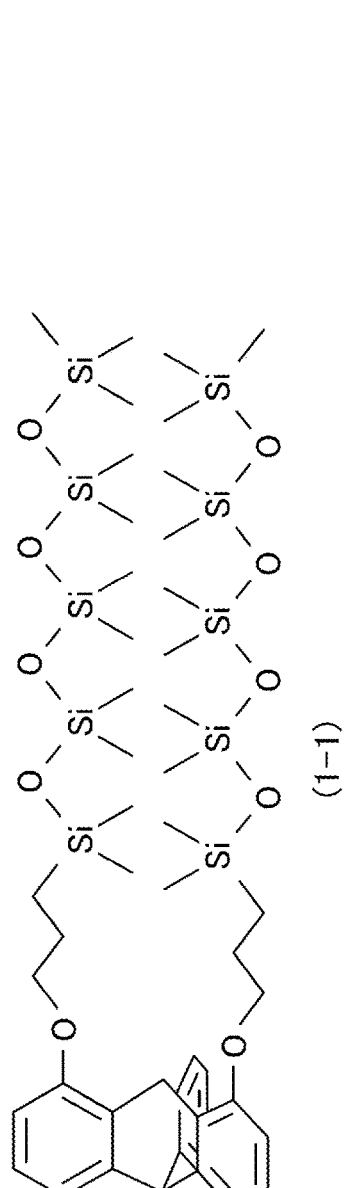
FIG. 8 is a diagram illustrating chemical structures of specific examples of the triptycene derivative represented by the general formula of FIG. 7.
Figure 8:
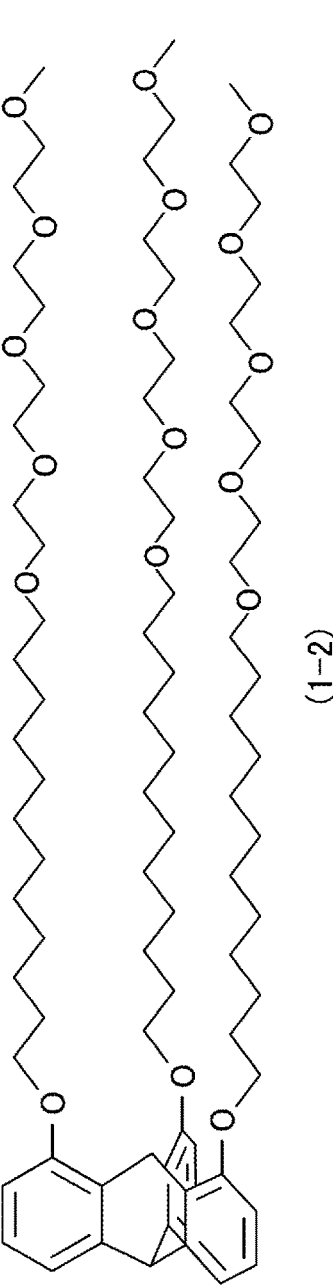
Figure 8:
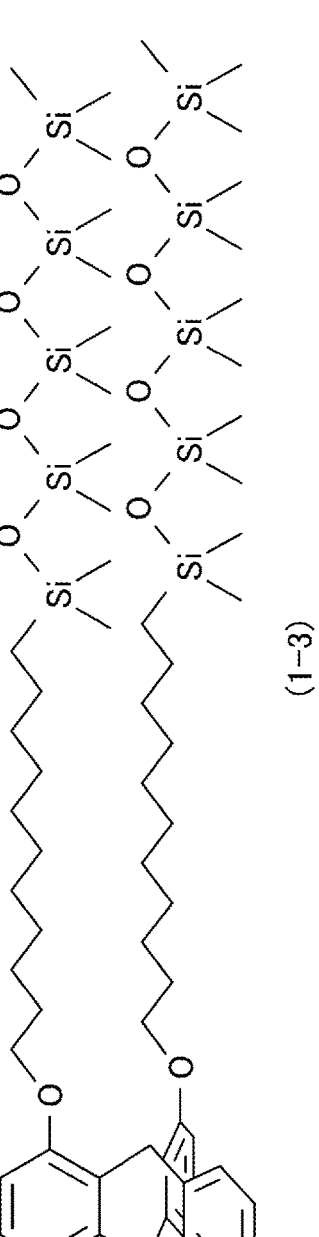

As the triptycene derivative represented by the general formula of FIG. 7, the above triptycene derivative in FIG. 6 and triptycene derivatives expressed by chemical formulae (1-1) to (1-3) in FIG. 8 are exemplified.

Also, in the present disclosure, the case in which the first side chain is included on the one plane side, which is the side of the one plane from among the first plane and the second plane, and the second side chain is included on the another plane side is specifically a case in which the first side chain is bonded to the triptycene skeleton at the one plane of the first plane and the second plane and the second side chain is bonded to the triptycene skeleton at the another plane of the first plane and the second plane. That is, the first side chain and the second side chain extend in opposite directions from the triptycene skeleton.

No particular limitation is imposed on the triptycene derivative having the structure in which the first side chain and the second side chain extend in opposite directions from the triptycene skeleton. As the triptycene derivative as described above, it is possible to use, for example, a triptycene derivative having the chemical structure of FIG. 9, i.e., a triptycene derivative in which the alkyl chain is bonded via oxygen (alkoxy group) to the first plane or the second plane of the triptycene skeleton, and the TEG chain is bonded to the first plane or the second plane that is a plane opposite to the plane to which the alkyl chain is bonded (see FIG. 9).

Figure 9:
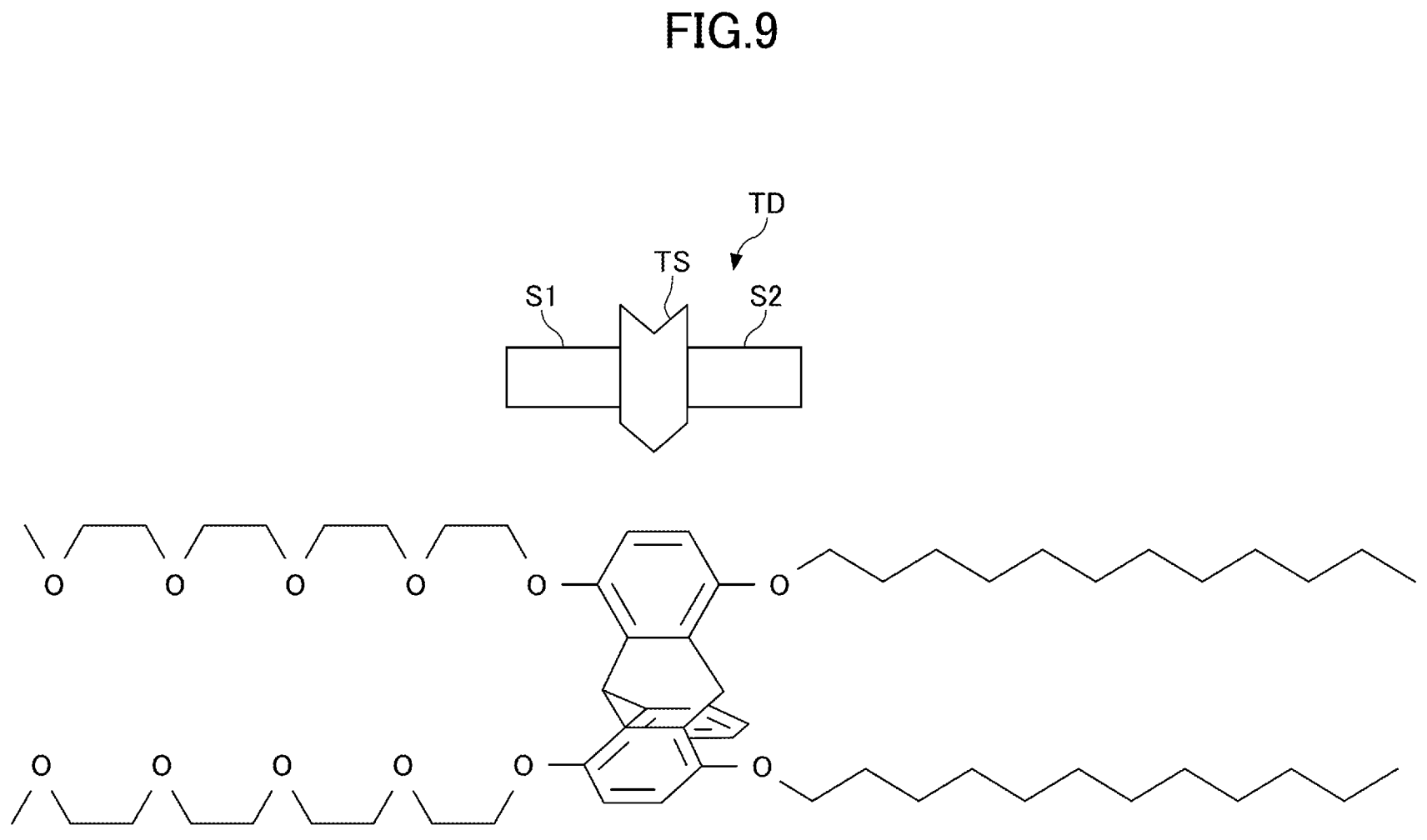

The triptycene derivative having the chemical structure as depicted in the lower part of FIG. 9 is a single molecule TD that is depicted as a schematic view in the upper part of FIG. 9. The single molecule TD of the triptycene derivative includes a triptycene skeleton TS, a first side chain S1 bonded to the first plane of the triptycene skeleton TS, and a second side chain S2 bonded to the second plane of the triptycene skeleton TS (see FIG. 9).

Figure 10:
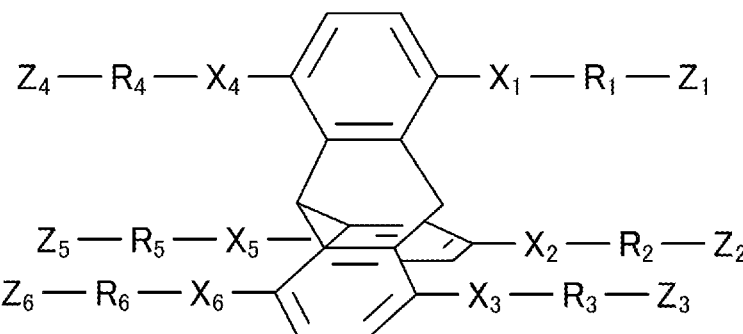
FIG. 10 is a diagram illustrating a general formula of a triptycene derivative having a structure including a first side chain and a second side chain extending from the triptycene skeleton in opposite directions.

Note that, the triptycene derivative having the structure in which the first side chain and the second side chain extend in opposite directions from the triptycene skeleton is represented by the general formula in FIG. 10. In the general formula of FIG. 10, $R_1$, $R_2$, and $R_3$ correspond to the first side chain, and $R_4$, Rr, and $R_6$ correspond to the second side chain.

In the formula of FIG. 10, $R_1$, $R_2$, and $R_3$ are the same group, and represent a saturated or unsaturated divalent hydrocarbon group having from 5 through 30 carbon atoms. This hydrocarbon group may have one substituent or two or more substituents. Also, one carbon atom or two or more carbon atoms in the hydrocarbon group may be substituted with an oxygen atom, a sulfur atom, a silicon atom, or —NR7-(where R7 represents a hydrogen atom, an alkyl group having from 1 through 10 carbon atoms, or an aryl group having from 6 through 30 carbon atoms).

Also, in the formula of FIG. 10, $R_4$, $R_5$, and $R_6$ are the same group and are groups different from $R_1$, $R_2$, and $R_3$, and represent a saturated or unsaturated divalent hydrocarbon group having from 5 through 30 carbon atoms. This hydrocarbon group may have one substituent or two or more substituents. Also, one carbon atom or two or more carbon atoms in the hydrocarbon group may be substituted with an oxygen atom, a sulfur atom, a silicon atom, or —NR8-(where R8 represents a hydrogen atom, an alkyl group having from 1 through 10 carbon atoms, or an aryl group having from 6 through 30 carbon atoms).

Note that, in the formula of FIG. 10, $X_1$, $X_2$, and $X_3$ are the same group, and are a linking group (or a linker group) formed of a divalent atomic group including: from 1 through 5 atoms selected from the group consisting of a nitrogen atom, an oxygen atom, a sulfur atom, a carbon atom, and a silicon atom; and a hydrogen atom.

Also, in the formula of FIG. 10, $Z_1$, $Z_2$, and $Z_3$ are the same group, and are an end group (or a terminal group) formed of a hydrogen atom or formed of a monovalent atomic group including: from 1 through 15 atoms selected from the group consisting of a nitrogen atom, an oxygen atom, a sulfur atom, a carbon atom, a phosphorus atom, a halogen atom, and a silicon atom; and a hydrogen atom.

Also, in the formula of FIG. 10, $Z_4$, $Z_5$, and $Z_6$ are the same group, and are an end group (or a terminal group) formed of a hydrogen atom or formed of a monovalent atomic group including: from 1 through 15 atoms selected from the group consisting of a nitrogen atom, an oxygen atom, a sulfur atom, a carbon atom, a phosphorus atom, a halogen atom, and a silicon atom; and a hydrogen atom.

Figure 11:
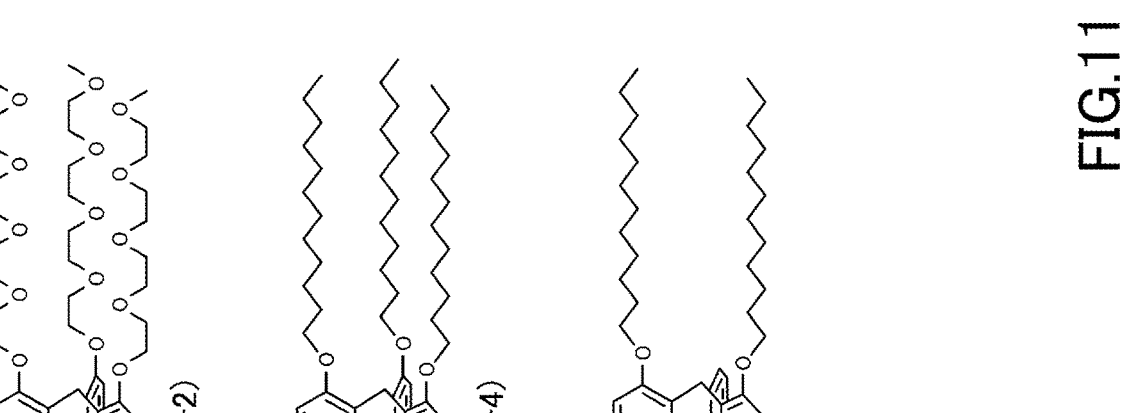
FIG. 11 is a diagram illustrating chemical structures of specific examples of the triptycene derivative represented by the general formula of FIG. 7.
Figure 11:
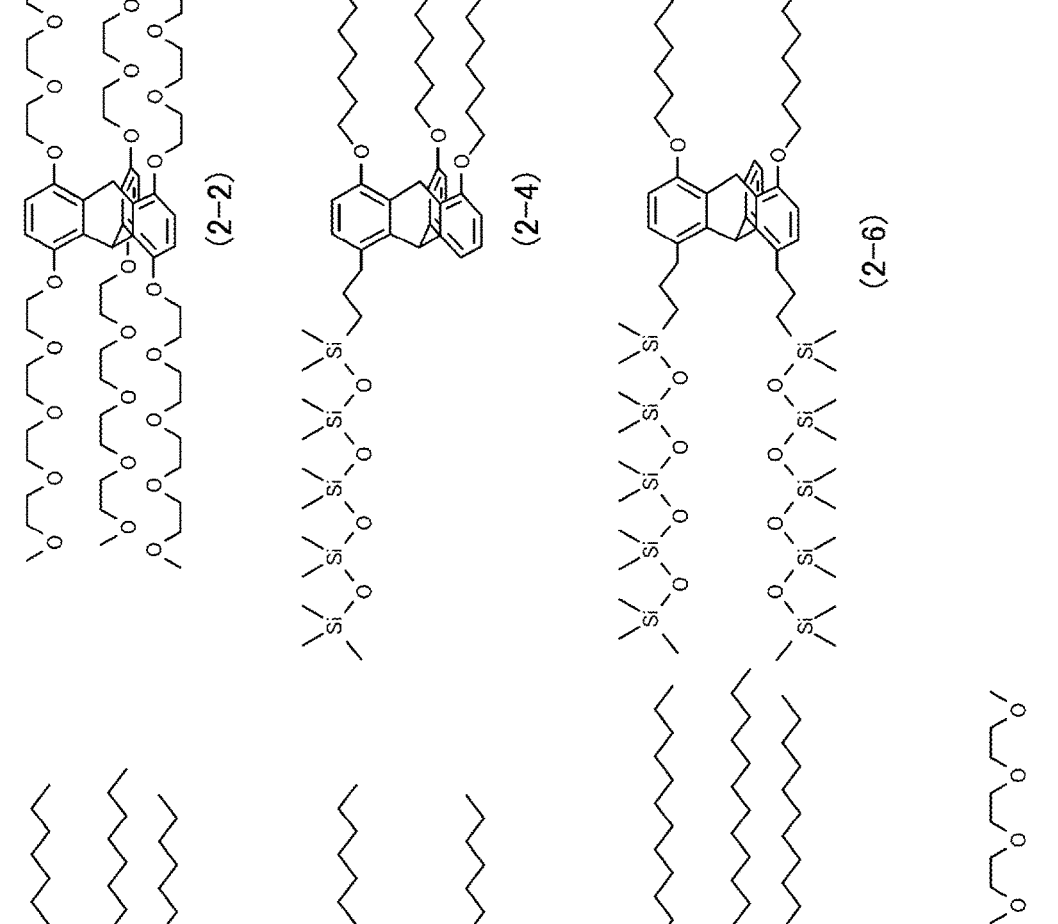
Figure 11:
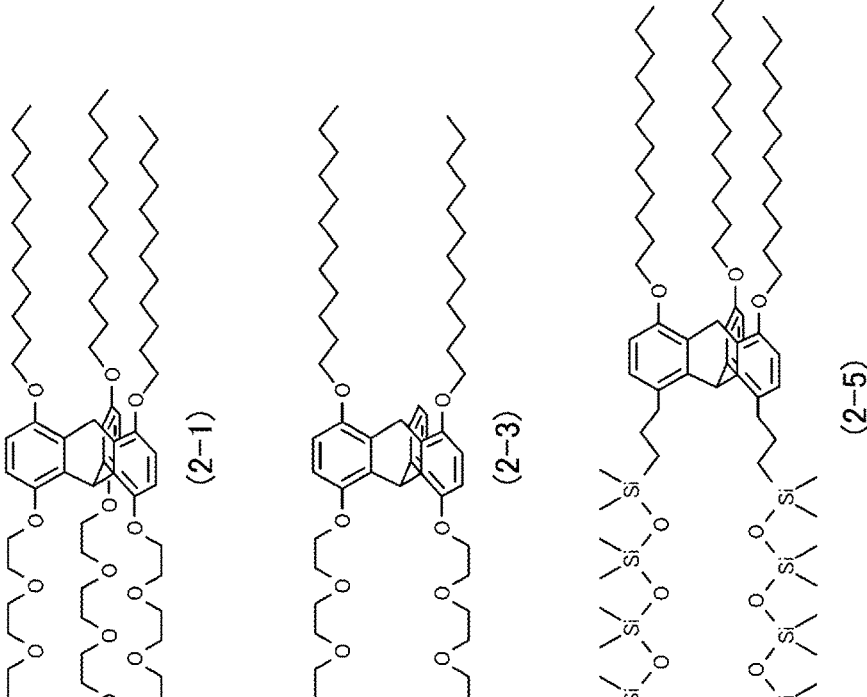
Figure 11:
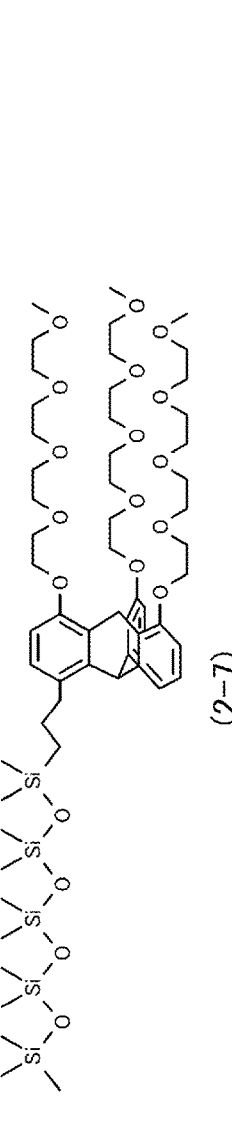
Figure 12:
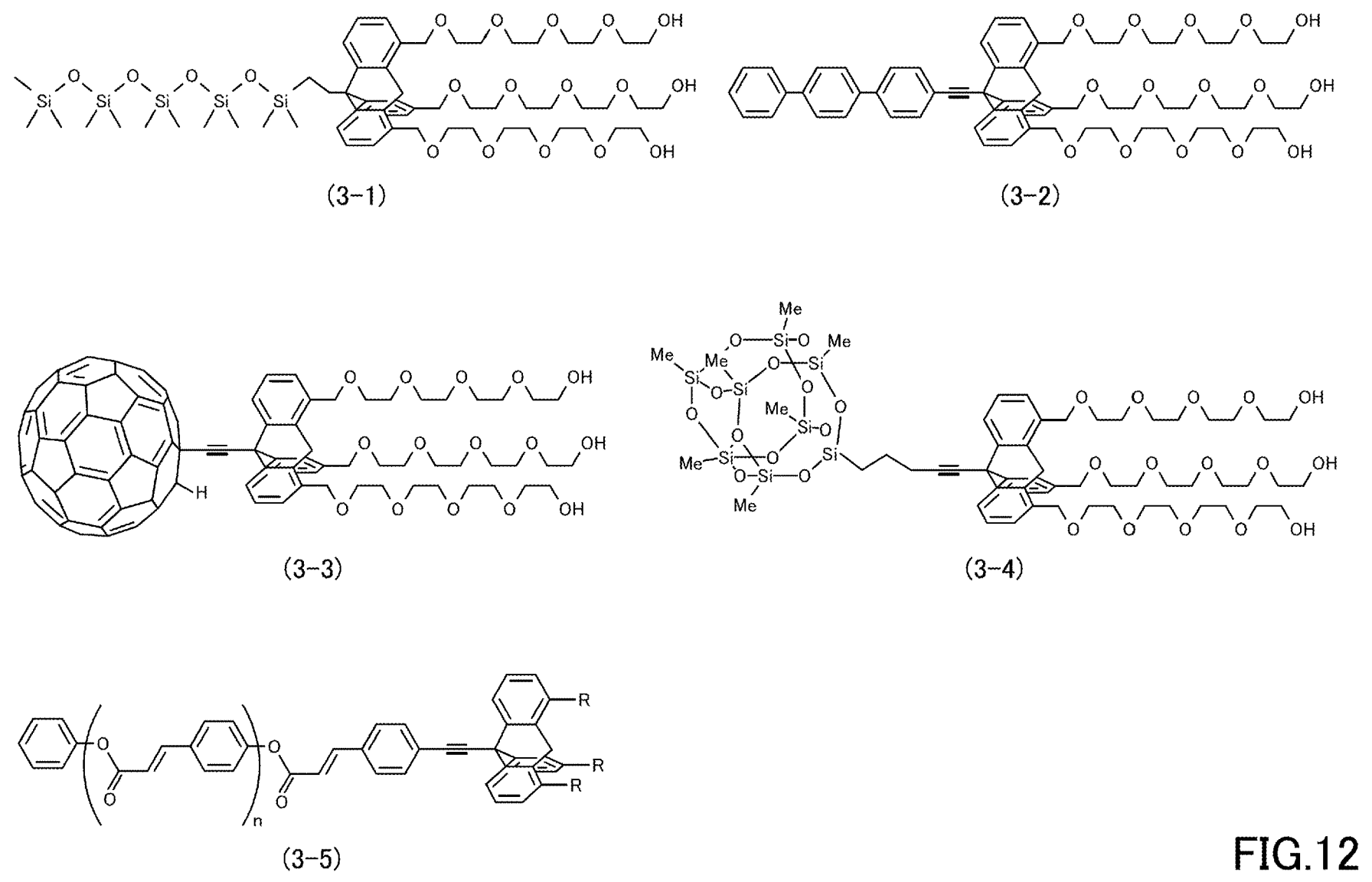

As the triptycene derivative represented by the general formula of FIG. 10, the above triptycene derivative in FIG. 9 and triptycene derivatives expressed by chemical formulae (2-1) to (2-7) in FIG. 11 are exemplified. Also, as the triptycene derivative represented by the general formula of FIG. 10, triptycene derivatives expressed by chemical formulae (3-1) to (3-5) in FIG. 12 are exemplified.

Figure 13:
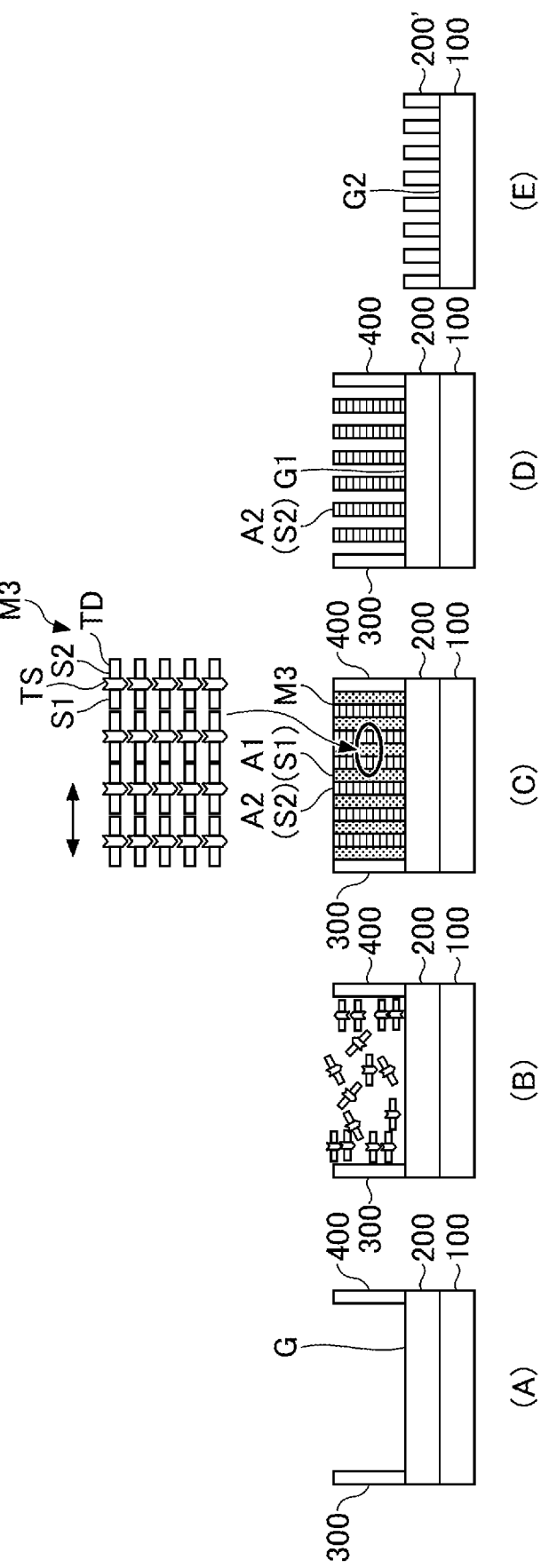
FIG. 13 is a view illustrating steps of forming a pattern using the triptycene derivative.

FIG. 13 illustrates steps of forming a resist pattern using the triptycene derivative. In (A) of FIG. 13, as an etching stop layer for silicon nitride or the like, two lateral walls (lateral walls 300 and 400) facing each other are stacked on a stack in which an insulating layer 200 such as a silicon oxide film or the like is stacked on a substrate 100 such as the single-crystal silicon or the like.

A space G (hereinafter may be referred to as a pattern groove) is formed inward of the lateral walls 300 and 400 forming the etching stop layer. For the space G, the distance (width) between the lateral walls 300 and 400 is adjusted to about 40 nm, and the height of the lateral walls 300 and 400 is adjusted to about 150 nm.

In (B) of FIG. 13, the above triptycene derivative is supplied to the space G inward of the lateral walls 300 and 400, and is formed into a film through vapor deposition, CVD, or the like. As a result, as illustrated in (C) of FIG. 13, a molecular assembly layer M3 of the triptycene derivative (three-dimensional assembly structure) is formed.

In the present embodiment, the triptycene derivative is supplied onto a pattern substrate provided with the lateral walls 300 and 400, followed by heating the pattern substrate, and then the melted triptycene derivative is developed on the pattern substrate by capillary action. In this state, further, the pattern substrate is gradually cooled, and as a result the triptycene derivative is recrystallized.

Note that, no limitation is imposed on the way of supplying the triptycene derivative onto the pattern substrate. For example, the triptycene derivative may be melted, with the triptycene derivative in the form of powder being placed on the pattern substrate obtained by processing silicon oxide ($SiO_2$). Also, the triptycene derivative may be vapor-deposited on the heated pattern substrate.

Also, no particular limitation is imposed on conditions for heating the pattern substrate. For example, the heating temperature can be a temperature that is higher than the melting point of the triptycene derivative by a temperature in the range of from about 10° C. through about 50° C. Also, the heating time can be a time in the range of from 30 minutes through 5 hours. In the present embodiment, the pattern substrate to which the triptycene derivative is supplied is heated for about 3 hours at a temperature that is higher by about 30° C. than the melting point of the triptycene derivative.

Also, no particular limitation is imposed on conditions for gradually cooling the pattern substrate. For example, the gradual cooling rate can be a rate in the range of from 0.1 through 3° C./min. Also, the gradual cooling time can be a time in the range of from 30 minutes through 5 hours. In the present embodiment, the pattern substrate on which the triptycene derivative is melted is cooled to room temperature at 3° C./min for about 2 hours.

Figure 14:
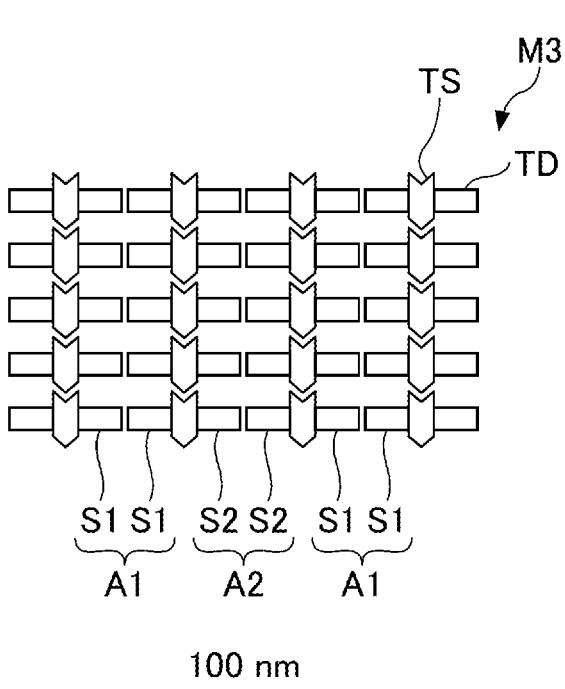
FIG. 14 is a view illustrating a state of a film formed through three-dimensional assembling of the triptycene derivative.

Note that, the schematic view in the upper part of (C) of FIG. 13, and FIG. 14 are an enlarged view of a part of the molecular assembly of the triptycene derivative. The molecular assembly layer M3 of the triptycene derivative has an assembly structure in which a plurality of single molecules TD of the triptycene derivative are aligned and assembled in the horizontal direction and the vertical direction. Here, being horizontal and being vertical include being approximately horizontal and being approximately vertical, respectively.

The molecular assembly layer M3 of the triptycene derivative has, for example, a structure in which the triptycene skeletons TS of the single molecule TD of the triptycene derivative are aligned in the vertical direction. Here, FIG. 15 to FIG. 18 depict specific examples of the assembly structure of the triptycene derivative in which the triptycene skeletons TS of the single molecule TD are aligned in the vertical direction.

Figure 15:
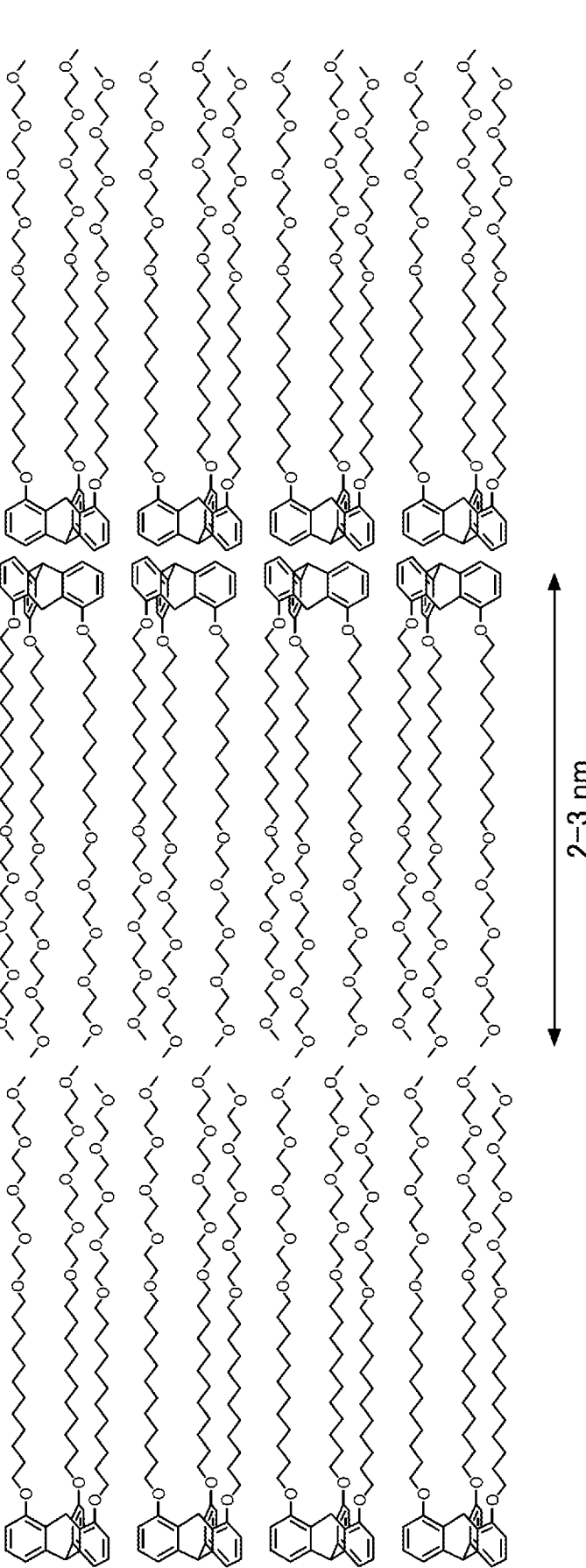
FIG. 15 is a view illustrating one example of an assembly structure of the triptycene derivative of FIG. 7.
Figure 16:
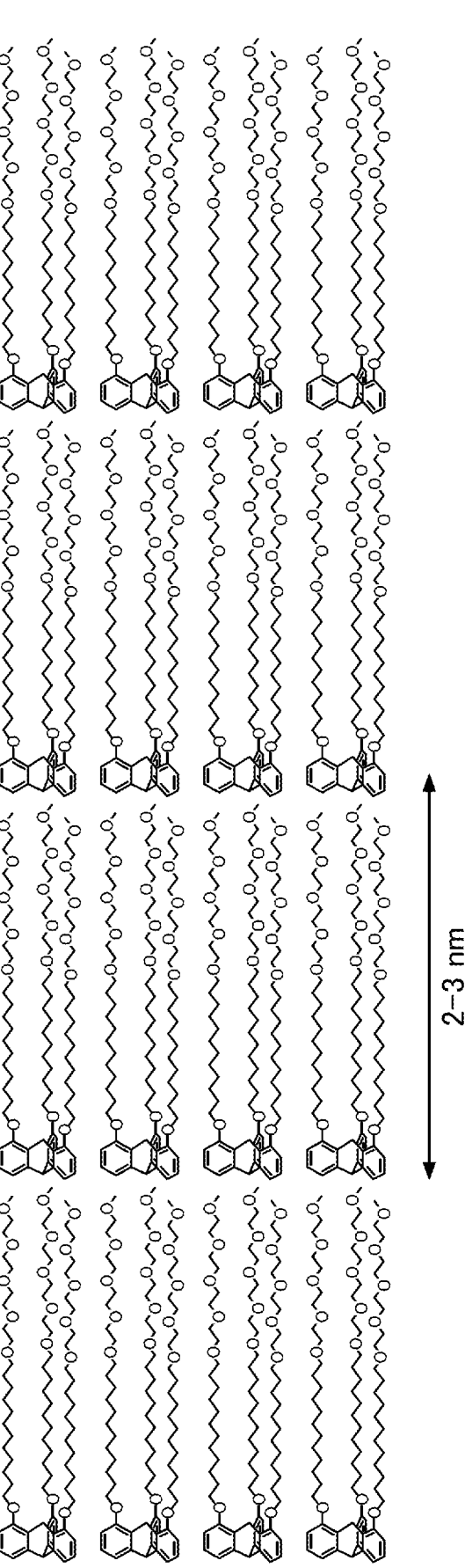
FIG. 16 is a view illustrating one example of an assembly structure of the triptycene derivative of FIG. 7.

Of these, FIG. 15 and FIG. 16 depict specific examples of the assembly structure of the triptycene derivative represented by the general formula of FIG. 7. In the assemblies of the single molecule TD of the triptycene derivative as depicted in FIG. 15 and FIG. 16, the alkyl chains as the first side chain S1 are bonded to the first plane or the second plane of the triptycene skeleton TS via the alkoxy group as the linking group, and the TEG chains as the second side chain S2 are bonded to the ends of the alkyl chains in series.

In the example as depicted in FIG. 15, the single molecules TD of the triptycene derivative are arranged in the molecular assembly layer M3 of the triptycene derivative so that the triptycene skeletons TS are aligned in the vertical direction and are next to each other in the horizontal direction. Also, the single molecules TD of the triptycene derivative are arranged so that the alkyl chains as the first side chain S1 are aligned in the vertical direction and the TEG chains as the second side chain S2 are aligned in the vertical direction and are next to each other in the horizontal direction.

In the example as depicted in FIG. 16, the single molecules TD of the triptycene derivative are arranged in the molecular assembly layer M3 of the triptycene derivative so that the triptycene skeletons TS are aligned in the vertical direction and are next to the TEG chains as the second side chain S2 in the horizontal direction. Also, the single molecules TD of the triptycene derivative are arranged so that the alkyl chains as the first side chain S1 are aligned in the vertical direction and the TEG chains as the second side chain S2 are aligned in the vertical direction.

Figure 17:
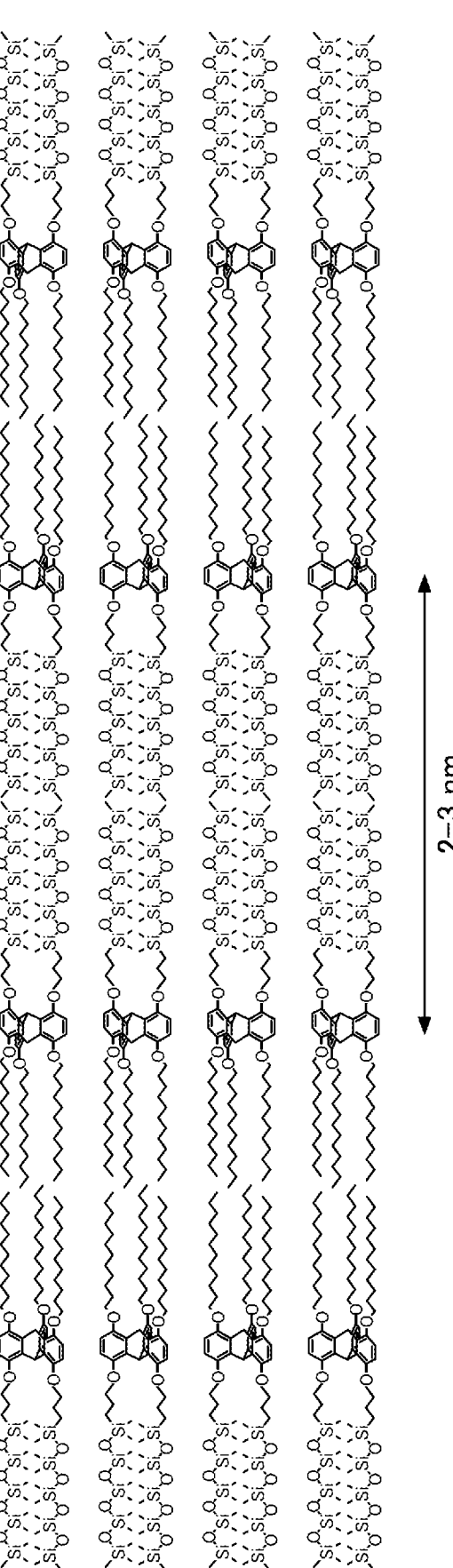
FIG. 17 is a view illustrating one example of an assembly structure of the triptycene derivative of FIG. 10.
Figure 18:
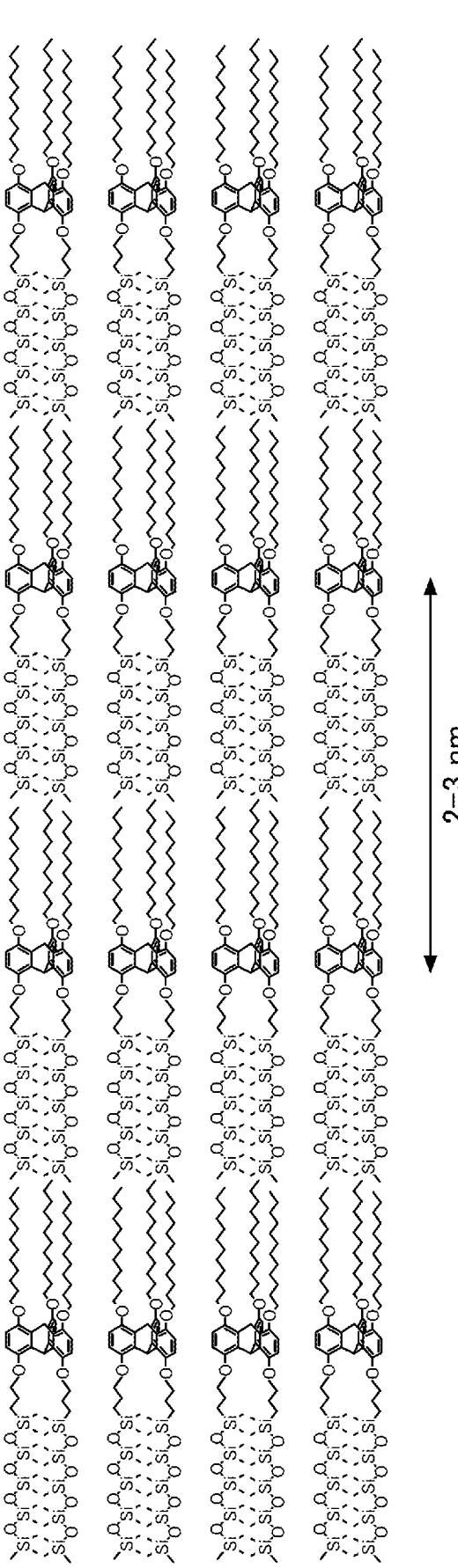
FIG. 18 is a view illustrating one example of an assembly structure of the triptycene derivative of FIG. 10.

FIG. 17 and FIG. 18 depict specific examples of the assembly structure of the triptycene derivative represented by the general formula of FIG. 10. In the assemblies of the single molecule TD of the triptycene derivative as depicted in FIG. 17 and FIG. 18, the alkyl chains as the first side chain S1 are bonded to the first plane of the triptycene skeleton TS via the alkoxy group as the linking group, and the DMS chains as the second side chain S2 are bonded to the second plane via the alkoxy group as the linking group.

In the example as depicted in FIG. 17, the single molecules TD of the triptycene derivative are arranged in the molecular assembly layer M3 of the triptycene derivative so that the alkyl chains as the first side chain S1 bonded to the triptycene skeletons TS are aligned in the vertical direction and are next to each other in the horizontal direction. Also, the single molecules TD of the triptycene derivative are arranged so that the DMS chains as the second side chain S2 are aligned in the vertical direction and are next to each other in the horizontal direction.

In the example as depicted in FIG. 18, the single molecules TD of the triptycene derivative are arranged in the molecular assembly layer M3 of the triptycene derivative so that the alkyl chains as the first side chain S1 bonded are aligned in the vertical direction and are next to the DMS chains as the second side chain S2 in the horizontal direction. Also, the single molecules TD of the triptycene derivative are arranged so that the DMS chains as the second side chain S2 bonded are aligned in the vertical direction and are next to the alkyl chains as the first side chain S1 in the horizontal direction.

Note that, the horizontal length of the single molecule TD of the triptycene derivative forming the molecular assembly layer M3 of the triptycene derivative as depicted in FIG. 15 to FIG. 18 is from about 2 through about 3 nm.

Thereby, the molecular assembly layer M3 of the triptycene derivative is formed, as the pattern film, inward of the lateral walls 300 and 400 in (C) of FIG. 13. The molecular assembly layer M3 of the triptycene derivative is, for example, a structure including an assembly A1 and an assembly A2 that are alternatingly arranged in the horizontal direction. The assembly A1 is a vertical stack of the first side chains S1. The assembly A2 is a vertical stack of the second side chains S2.

In the molecular assembly layer M3 of the triptycene derivative, the horizontal thickness of the assembly A1 of the first side chains S1 is 100 nm or larger, and the horizontal thickness of the assembly A2 of the second side chains S2 is 100 nm or larger.

Also, in the present embodiment, an aspect ratio of an inner region of the lateral walls 300 and 400 in (C) of FIG. 13 is adjusted to 2 or more. Here, the aspect ratio of the inner region of the lateral walls 300 and 400 indicates a ratio of a vertical dimension (depth) to a horizontal dimension (width) of the space G formed inward of the lateral walls 300 and 400.

In the present embodiment, the ratio of the height of the lateral walls 300 and 400 to the distance between the lateral walls 300 and 400 is 2 or more, and thus the aspect ratio of the pattern film formed inward of the lateral walls 300 and 400 as the molecular assembly layer M3 of the triptycene derivative is also 2 or more.

Specifically, in the molecular assembly layer M3 of the triptycene derivative, the assembly A1 of the first side chains S1, which are alternatingly arranged in the horizontal direction, and the assembly A2 of the second side chains S2, which are alternatingly arranged in the horizontal direction, are stacked so that the dimensions thereof in the vertical direction (stacking direction) are twice or more the dimensions thereof in the horizontal direction.

In the present embodiment, in a state in which the assembly A1 of the first side chains S1 and the assembly A2 of the second side chains S2 are stacked in the horizontal direction, the molecular assembly layer M3 of the triptycene derivative is formed in the inner region of the lateral walls 300 and 400. This molecular assembly layer M3 of the triptycene derivative is adjusted, correspondingly to the space G, to 150 nm in the vertical dimension (height) (the height of the lateral walls 300 and 400) and 40 nm in the horizontal dimension (width) (the distance between the lateral walls 300 and 400).

In (D) of FIG. 13, an etching treatment is performed to the molecular assembly layer M3 of the triptycene derivative formed in the inner region of the lateral walls 300 and 400, and the assembly A1 of the first side chains S1 is etched and the assembly A2 of the second side chains S2 having etching resistance remains. A space G1 is formed between the assemblies A2 of the second side chains S2. The horizontal thickness of the assembly A2 of the second side chains S2 is 10 nm or smaller, and a fine pattern film having etching resistance (e.g., a protective film) can be formed.

In (D) of FIG. 13, the assemblies A2 of the second side chains S2 serve as the protective films, and parts of the insulating layer 200 that are directly below the spaces G1 are further etched. Subsequently, by removing the assemblies A2 of the second side chains S2, insulating layers 200' are formed on the substrate 100, and spaces G2 are formed between the insulating layers 200'. The horizontal thickness of the space G2 between one insulating layer 200' and another insulating layer 200' is 10 nm or smaller, and a fine pattern can be formed on the substrate 100.

Figure 19:
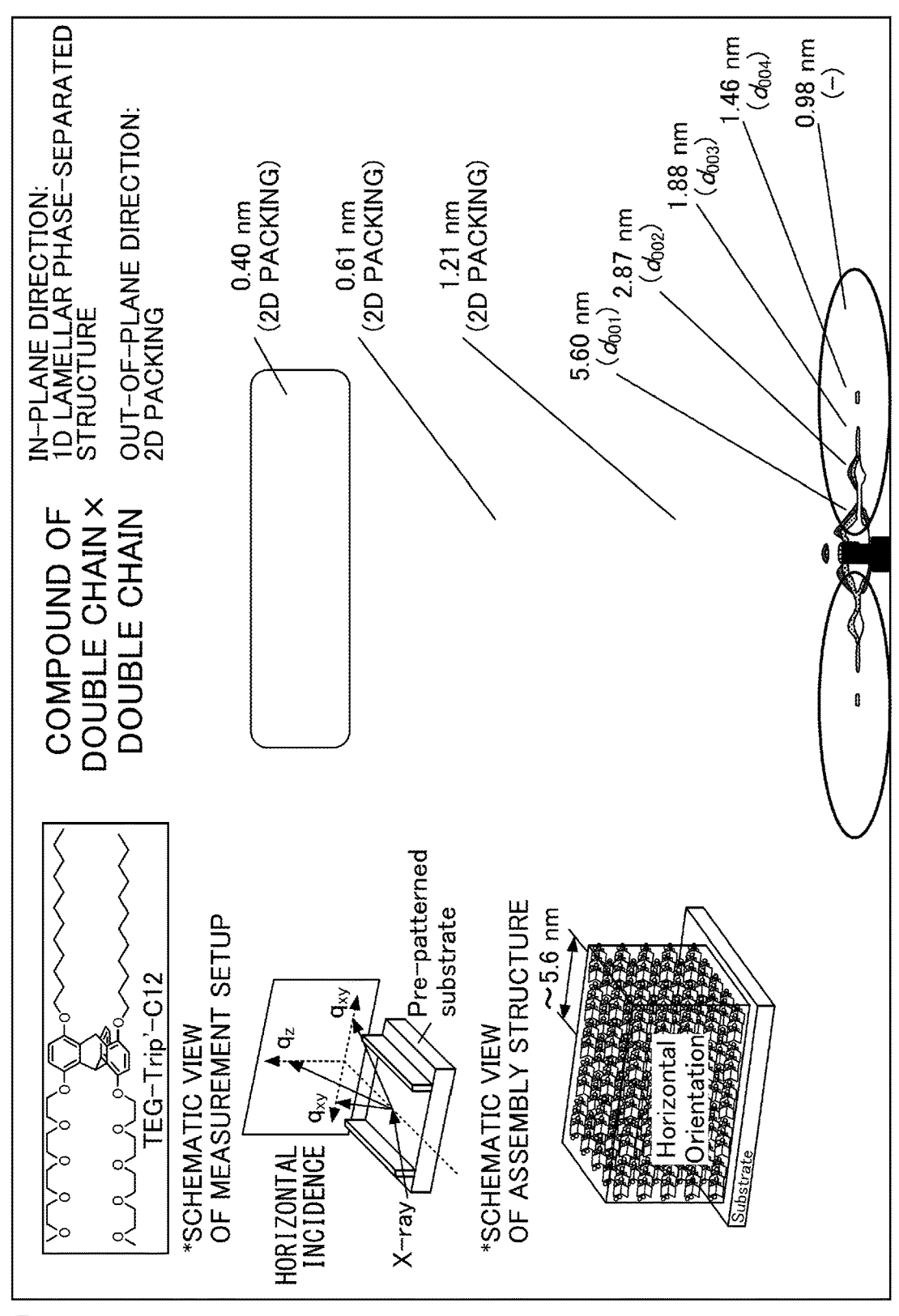
FIG. 19 is a representation illustrating results obtained through structural analysis by X-ray diffraction of the triptycene derivative (diffraction in an in-plane direction).

FIG. 19 is a representation illustrating results (diffraction in the in-plane direction) obtained through structural analysis by X-ray diffraction of the molecular assembly of the triptycene derivative depicted in FIG. 9 (chemical formula (2-3) of FIG. 11). In this structural analysis, diffraction attributed to the lamellar structure forming the molecular assembly of the triptycene derivative appears in the in-plane (horizontal) direction.

The diffraction results in FIG. 19 indicate that by using the triptycene derivative expressed by chemical formula (2-3) of FIG. 11, it is possible to obtain a pattern film having a structure in which assemblies of the first side chains stacked in the vertical direction and assemblies of the second side chains stacked in the vertical direction are alternatingly arranged in the horizontal direction.

Figure 20:
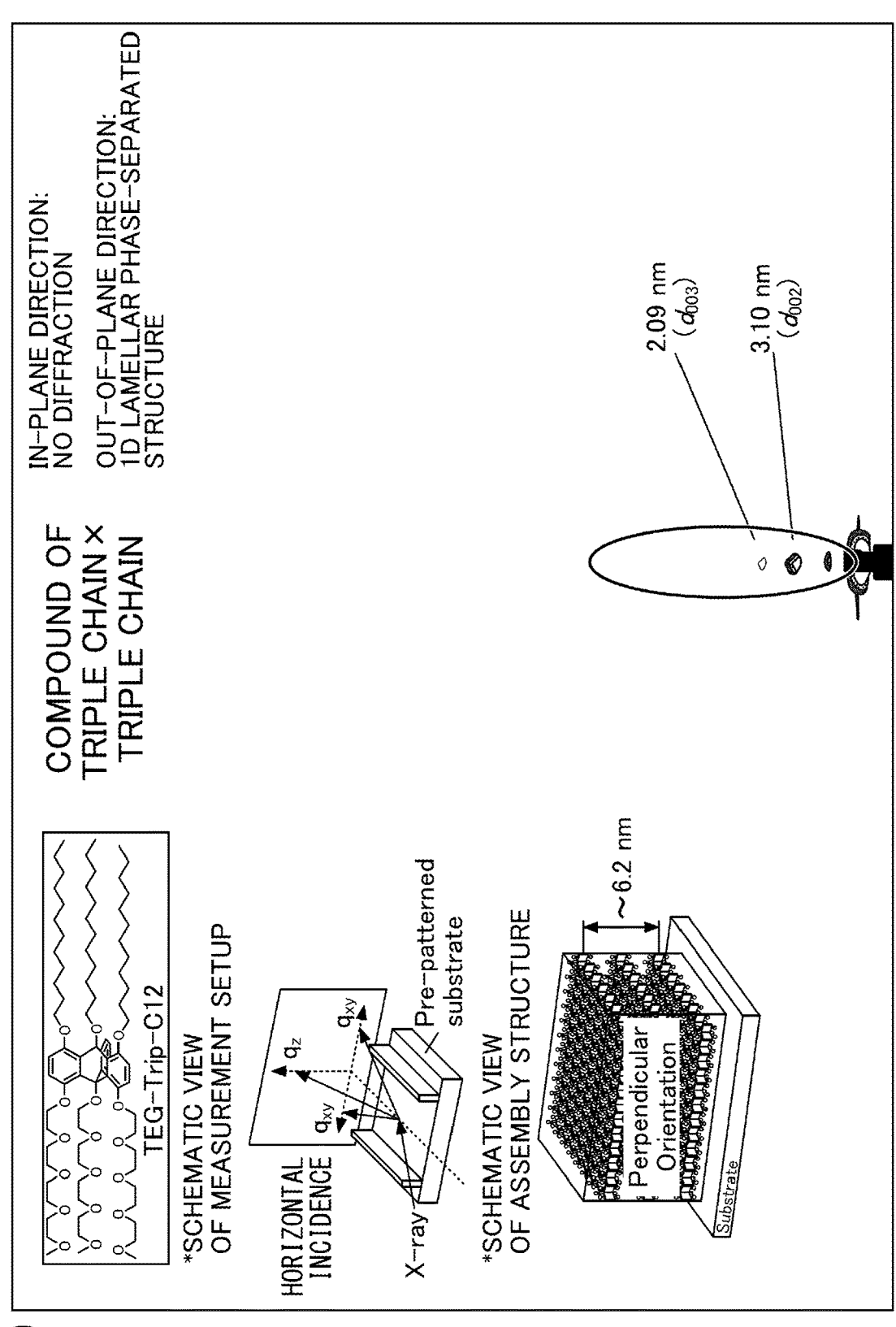
FIG. 20 is a representation illustrating results obtained through structural analysis by X-ray diffraction of the triptycene derivative (diffraction in an out-of-plane direction).

Also, FIG. 20 is a representation illustrating results (diffraction in the out-of-plane direction) obtained through structural analysis by X-ray diffraction of the molecular assembly of the triptycene derivative expressed by chemical formula (2-1) of FIG. 11. In this structural analysis, diffraction attributed to the lamellar structure forming the molecular assembly of the triptycene derivative appears in the out-of-plane (vertical) direction.

The diffraction results in FIG. 20 indicate that by using the triptycene derivative expressed by chemical formula (2-1) of FIG. 11, it is possible to obtain a pattern film having a structure in which assemblies of the first side chains stacked in the horizontal direction and assemblies of the second side chains stacked in the horizontal direction are alternatingly stacked in the vertical direction.

In this way, the structural analyses of FIG. 19 and FIG. 20 indicate that by appropriately selecting the type of the triptycene derivative, it is possible to control the stacking direction of the lamellar structure forming the molecular assembly of the triptycene derivative.

As described above, the pattern forming method of the present disclosure forms a pattern film including the triptycene derivative. The triptycene derivative includes the triptycene skeleton, the first side chain on the one plane side, which is the side of the one plane from among the first plane and the second plane of the triptycene skeleton, and the second side chain on the another plane side, which is the side of the another plane from among the first plane and the second plane, or on the one plane side, the second side chain having an etching selectivity ratio different from the etching selectivity ratio of the first side chain.

Thereby, according to the pattern forming method of the present disclosure, the obtained molecular assembly layer of the triptycene derivative can form a lamellar structure in which assemblies of the first side chains stacked in the vertical or horizontal direction and assemblies of the second side chains stacked in the vertical or horizontal direction are alternatingly stacked in the horizontal or vertical direction.

Also, in such a lamellar structure, the horizontal or vertical thickness of the assembly of the first side chains can be 10 nm or smaller, and the horizontal thickness of the assembly of the second side chains can be 10 nm or smaller. Therefore, the present disclosure can form a fine pattern structure having etching resistance.

According to the pattern forming method of the present disclosure, as described above, the first side chains are bonded to the triptycene skeleton, and the second side chains are bonded to the ends of the first side chains (FIG. 6 to FIG. 8). Thereby, the obtained pattern film can form a dense pattern structure in which the assemblies of the first side chains stacked in the vertical direction and the assemblies of the second side chains stacked in the vertical direction are alternatingly arranged in the horizontal direction with a thickness of 10 nm or smaller (FIG. 15 and FIG. 16).

According to the pattern forming method of the present disclosure, as described above, the first side chains are bonded to the triptycene skeleton on the one plane side, and the second side chains are bonded to the triptycene skeleton on the another plane side (FIG. 9 to FIG. 12). Thereby, the obtained pattern film can form a dense pattern structure in which the assemblies of the first side chains stacked in the vertical direction and the assemblies of the second side chains stacked in the vertical direction are alternatingly arranged in the horizontal direction with a thickness of 10 nm or smaller (FIG. 17 and FIG. 18).

As described above, the pattern forming method of the present disclosure forms the pattern film in the inner region of the two facing lateral walls. Thereby, the present disclosure can form, in a limited area, the dense pattern structure in which the assemblies of the first side chains stacked in the vertical direction and the assemblies of the second side chains stacked in the vertical direction are alternatingly arranged in the horizontal direction with a thickness of 10 nm or smaller (see FIG. 13).

Also, as described above, by heating the pattern substrate to which the triptycene derivative is supplied, followed by gradually cooling, the triptycene derivative recrystallized on the pattern substrate can form the densely self-assembled molecular assembly layer (three-dimensional assembly structure) M3.

Note that, as described above, when the triptycene derivative is vapor-deposited on the pattern substrate, voids tend to form in the pattern substrate. Meanwhile, in the present embodiment, the triptycene derivative is vapor-deposited on the heated pattern substrate, and the triptycene derivative is melted and deposited in the pattern groove. The subsequent heating and gradual cooling form the self-assembled dense molecular assembly layer, and thus formation of voids can be suppressed.

According to the pattern forming method of the present disclosure, as described above, the aspect ratio of the pattern film is 2 or more, and a plurality of fine pattern structures that are narrow and long in the vertical direction can be formed in the limited inner area of the lateral walls.

According to the pattern forming method of the present disclosure, as described above, one side chain from among the first side chain and the second side chain has an inorganic composition, and the pattern film formed as the assembly of the vertically stacked side chains having the inorganic composition can function as the protective film having etching resistance.

Also, according to the pattern forming method of the present disclosure, as described above, the inorganic composition forming the side chain that is the first side chain or the second side chain includes a siloxane compound. Thus, even if the side chain of the triptycene skeleton has the inorganic composition, the boiling point of the triptycene derivative can be reduced. Therefore, according to the pattern forming method of the present disclosure, it is possible to reduce the temperature for film formation.

According to the pattern forming method of the present disclosure, as described above, the first side chain or the second side chain has an organic composition, and the fine pattern film formed as the assembly of the vertically stacked side chains having the organic composition can function as the etching film.

According to the pattern forming method of the present disclosure, as described above, by hydroxy-terminating the end of the first side chain or the second side chain having the organic composition, it is possible to form a hydrogen bond at the end of the first side chain or the second side chain. Thereby, it is possible to increase the melting point of the triptycene derivative in which the end of the first side chain or the second side chain having the organic composition is hydroxy-terminated. Therefore, according to the pattern forming method of the present disclosure, the obtained pattern film can have an increased heat stability.

Figure 21:
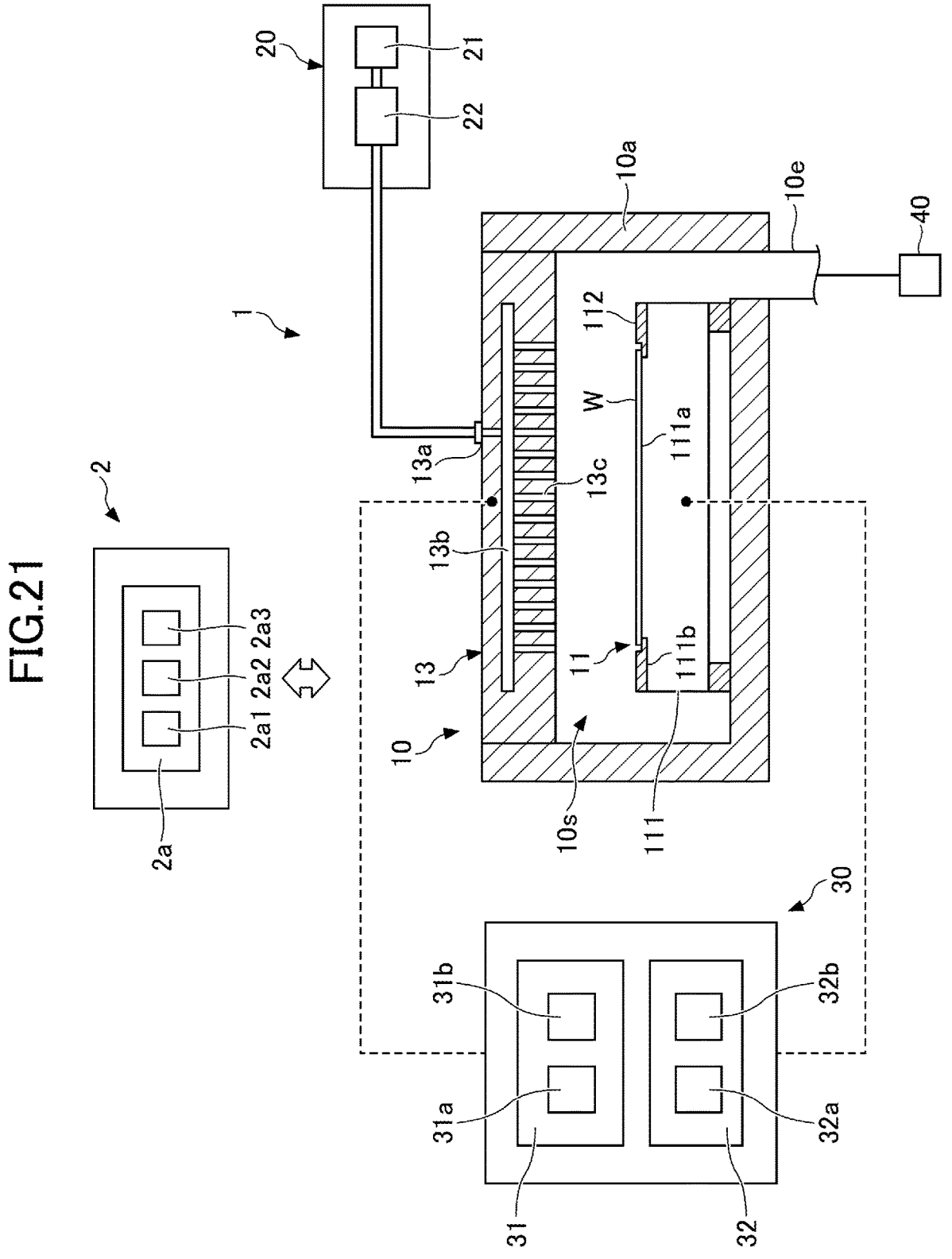
FIG. 21 is a view illustrating a plasma processing system for performing a plasma processing method that is one example of the pattern forming method.

By utilizing such configurations and effects, the pattern forming method of the present disclosure can be applied to a plasma processing method. FIG. 21 is a view illustrating a plasma processing system for performing the plasma processing method that is one example of the pattern forming method according to the present disclosure. Hereinafter, an embodiment of the plasma processing system will be described.

The plasma processing system includes a capacitive coupling plasma processing device 1 and a controller 2.

The capacitive coupling plasma processing device 1 includes a plasma processing chamber 10, a gas supply 20, a power supply 30, and an exhausting system 40. Also, the plasma processing device 1 includes a substrate support 11 and a gas introducer. The gas introducer is configured to introduce a processing gas into the plasma processing chamber 10. The gas introducer includes a shower head 13.

Here, the processing gas includes various gases. For example, when the pattern film is formed on the below-described substrate W, a film-forming gas including the above triptycene derivative is included. Also, when the pattern film is etched, an etching gas such as an oxygen-based gas, a CF (fluorocarbon)-based gas, or the like is included. Moreover, an inert gas such as an argon gas, a nitrogen gas, or the like is included as a carrier gas upon forming or etching the pattern film.

The substrate support 11 is disposed in the plasma processing chamber 10. The shower head 13 is disposed above the substrate support 11. In the present embodiment, the shower head 13 forms at least a part of the ceiling of the plasma processing chamber 10. The plasma processing chamber 10 includes the shower head 13 and a plasma processing space 10s that is defined by a lateral wall 10a of the plasma processing chamber 10 and by the substrate support 11.

The plasma processing chamber 10 includes at least one gas supplying port from which the processing gas is supplied to the plasma processing space 10s, and at least one gas exhausting port from which the gas is exhausted from the plasma processing space. The lateral wall 10a is grounded. The shower head 13 and the substrate support 11 are electrically insulated from a casing of the plasma processing chamber 10.

The substrate support 11 includes a body 111 and a ring assembly 112. The body 111 includes a center region (substrate support surface) 111a where the substrate (wafer) W is supported, and an annular region (ring support surface) 111b where the ring assembly 112 is supported.

Note that, as the substrate (wafer) W supported in the center region (substrate support surface) 111a, for example, the above-described pattern substrate provided with the lateral walls 300 and 400 is used.

The annular region 111b of the body 111 encloses the center region 11a of the body 111 in a plan view thereof. The substrate W is disposed on the center region 111a of the body 111. Also, the ring assembly 112 is disposed on the annular region 111b of the body 111 so as to enclose the substrate W on the center region 111a of the body 111.

Note that, the substrate support 11 may be provided with a heater (not illustrated) configured to heat the center region 111a of the body 111. The substrate W disposed on the center region 111a can be heated by such a heater, and thus heat treatments such as vapor deposition, heating, or the like of the triptycene derivative supplied to the substrate W can be performed.

In the present embodiment, the body 111 includes a base plate and an electrostatic chuck. The base plate includes a conductive member. The conductive member of the base plate functions as a lower electrode. The electrostatic chuck is disposed on the base plate. The upper surface of the electrostatic chuck includes the substrate support surface 111a.

The ring assembly 112 includes one or more annular members. At least one of the one or more annular members is an edge ring. Also, although not illustrated, the substrate support 11 may include a temperature controlling module configured to control the electrostatic chuck, the ring assembly 112, the substrate, or any combination thereof, to the target temperature.

The temperature controlling module may include a heater, a heat conducting medium, a flow path, or any combination thereof. Such a heat conducting fluid as brine or gas flows through the flow path. Also, the substrate support 11 may include a heat conducting gas supply configured to supply a heat conducting gas between the back surface of the substrate W and the substrate support surface 111a.

The shower head 13 is configured to introduce the processing gas from the gas supply 20 into the plasma processing space 10s. The shower head 13 includes at least one gas supplying port 13a, at least one gas diffusing chamber 13b, and a plurality of gas introducing ports 13c. The processing gas introduced to the gas supplying port 13a passes through the gas diffusing chamber 13b and is introduced into the plasma processing space 10s from the plurality of gas introducing ports 13c.

Also, the shower head 13 includes a conductive member. The conductive member of the shower head 13 functions as an upper electrode. Note that, the gas introducer may include, in addition to the shower head 13, one or more side gas injectors (SGIs) attached to one or more openings formed in the lateral wall 10a.

The gas supply 20 may include at least one gas source 21 and at least one flow rate controller 22. In the present embodiment, the gas supply 20 is configured to supply the processing gas to the shower head 13 from the gas source 21 via the corresponding flow rate controller 22. The flow rate controller 22 may include a mass flow controller, a pressure-controlled flow rate controller, or the like.

Moreover, the gas supply 20 may include one or more flow rate modulating devices configured to modulate the flow rate of the processing gas, or form it into pulses.

The power supply 30 includes a RF power supply 31 connected to the plasma processing chamber 10 via at least one impedance matching circuit. The RF power supply 31 is configured to supply at least one RF signal (RF power), such as a source RF signal and a bias RF signal, to the conductive member of the substrate support 11 and/or the conductive member of the shower head 13. Thereby, a plasma is generated from the processing gas supplied to the plasma processing space 10s.

Therefore, the RF power supply 31 can function as at least a part of a plasma generator configured to generate the plasma from the processing gas in the plasma processing chamber 10. Also, by supplying the bias RF signal to the conductive member of the substrate support 11, a bias potential is generated in the substrate W, and ionic components in the formed plasma can be taken into the substrate W.

In the present embodiment, the RF power supply 31 includes a first RF generator 31a and a second RF generator 31b. The first RF generator 31a is connected to the conductive member of the substrate support 11 and/or the conductive member of the shower head 13 via at least one impedance matching circuit, and is configured to generate the source RF signal (source RF power) for plasma generation.

In the present embodiment, the source RF signal has a frequency in the range of from 13 MHz through 150 MHz.

In the present embodiment, the first RF generator 31*a* may be configured to generate a plurality of source RF signals having different frequencies. The one or more source RF signals generated are supplied to the conductive member of the substrate support 11 and/or the conductive member of the shower head 13.

The second RF generator 31*b* is connected to the conductive member of the substrate support 11 via at least one impedance matching circuit, and is configured to generate a bias RF signal (bias RF power). In the present embodiment, the bias RF signal has a frequency lower than the frequency of the source RF signal. In the present embodiment, the bias RF signal has a frequency in the range of from 400 kHz through 13.56 MHz.

In the present embodiment, the second RF generator 31*b* may be configured to generate a plurality of bias RF signals having different frequencies. The one or more bias RF signals generated are supplied to the conductive member of the substrate support 11. Also, in various embodiments, the source RF signal, the bias RF signal, or both may be formed into pulses.

Also, the power supply 30 may include a DC power supply 32 connected to the plasma processing chamber 10. The DC power supply 32 includes a first DC generator 32*a* and a second DC generator 32*b*.

In the present embodiment, the first DC generator 32*a* is connected to the conductive member of the substrate support 11, and is configured to generate a first DC signal. The first bias DC signal generated is applied to the conductive member of the substrate support 11. In the present embodiment, the first DC signal may be applied to another electrode such as an electrode in the electrostatic chuck.

In the present embodiment, the second DC generator 32*b* is connected to the conductive member of the shower head 13, and is configured to generate a second DC signal. The second DC signal generated is applied to the conductive member of the shower head 13.

In various embodiments, the first DC signal, the second DC signal, or both may be formed into pulses. Note that, the first and second DC generators 32*a* and 32*b* may be provided in addition to the RF power supply 31, or the first DC generator 32*a* may be provided instead of the second RF generator 31*b*.

For example, the exhausting system 40 may be connected to a gas exhausting port 10*e* provided in the bottom of the plasma processing chamber 10. The exhausting system 40 may include a pressure adjusting valve and a vacuum pump. By the pressure adjusting valve, the pressure in the plasma processing space 10*s* is adjusted. The vacuum pump may include a turbomolecular pump, a dry pump, or a combination thereof.

A controller 2 processes computer-executable commands that cause the plasma processing device 1 to execute various steps described in the present disclosure. The controller 2 may be configured to control the components of the plasma processing device 1 so as to execute various steps described herein. In the present embodiment, the controller 2 may be partially or entirely included in the plasma processing device 1.

The controller 2 may include a computer 2*a* and the like. The computer 2*a* may include a processor (CPU: Central Processing Unit) 2*al*, a storage 2*a2*, and a communication interface 2*a3*. The processor 2*al* may be configured to perform control operations based on programs stored in the storage 2*a2*.

The storage 2*a2* may include a RAM (Random Access Memory), a ROM (Read Only Memory), a HDD (Hard Disk Drive), a SSD (Solid State Drive), or any combination thereof. The communication interface 2*a3* may communicate with the plasma processing device 1 via a communication line such as a LAN (Local Area Network) or the like.

Figure 22:
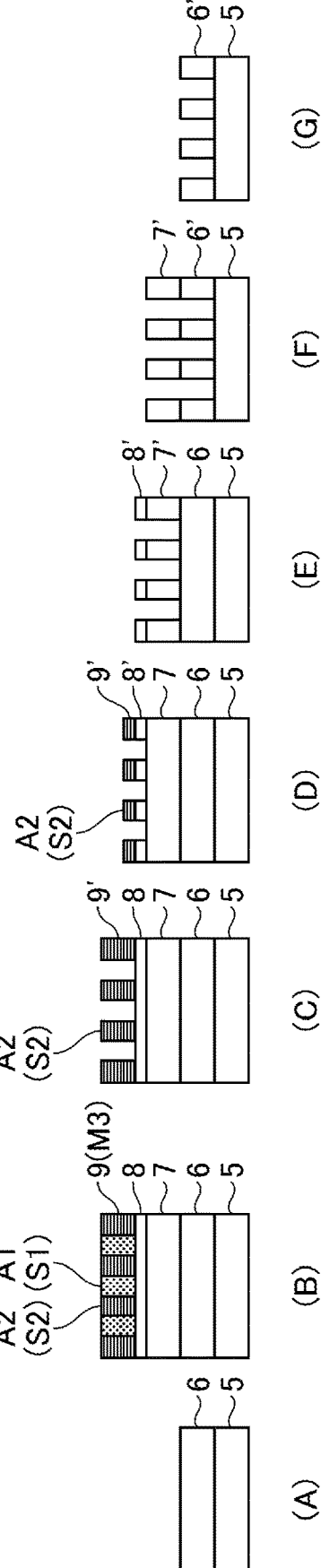
FIG. 22 is a view illustrating steps of forming a pattern through plasma etching using the triptycene derivative.

In the present embodiment, steps (A) to (G) in FIG. 22 are performed by using the above-described plasma processing system. That is, the pattern film including the above-described triptycene derivative is formed on the surface of the substrate W, and the pattern film is etched with a plasma treatment.

In (A) of FIG. 22, an insulating layer 6 is stacked on a substrate 5.

In (B) of FIG. 22, protective layers 7 and 8 are stacked in order on the insulating layer 6, and moreover, a pattern film 9 including the triptycene derivative (the molecular assembly layer M3 of the triptycene derivative) is formed thereon.

In (C) of FIG. 22, the assembly A1 of the first side chains S1 in the pattern film 9 is etched, thereby forming a pattern film 9' in which the assembly A2 of the second side chains S2 remains.

In (D) of FIG. 22, the pattern film 9' serves as the protective film, and the protective layer 8 is etched to form a protective layer 8'.

In (E) of FIG. 22, the pattern film 9' is removed, and while the protective layer 8' protects a part of the protective layer 7, the protective layer 7 is etched to form a protective layer 7'.

In (F) of FIG. 22, while the protective layer 7' protects a part of the insulating layer 6, the insulating layer 6 is etched to form an insulating layer 6'.

In (G) of FIG. 22, the protective layer 7' is removed, thereby forming a pattern of the insulating layer 6' on the substrate 5. The obtained pattern can be used as a resist pattern.

Figure 23:
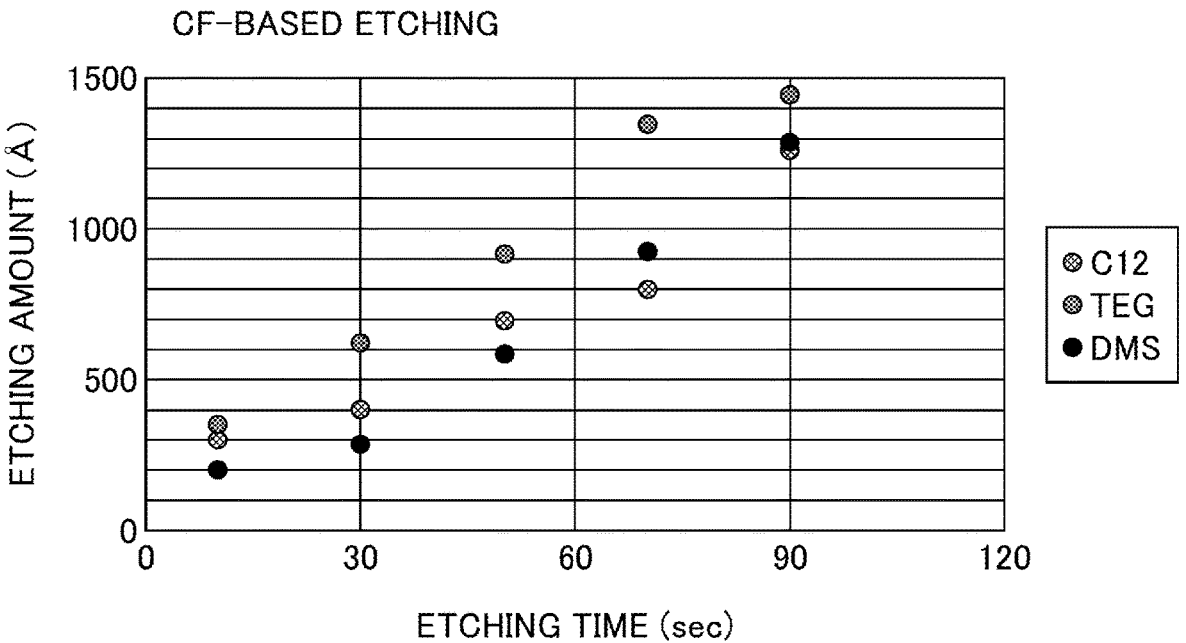
FIG. 23 is a view illustrating a relationship between an etching time and an etching amount for the side chains of the triptycene derivative when a CF-based etching is performed in FIG. 22.
Figure 25:
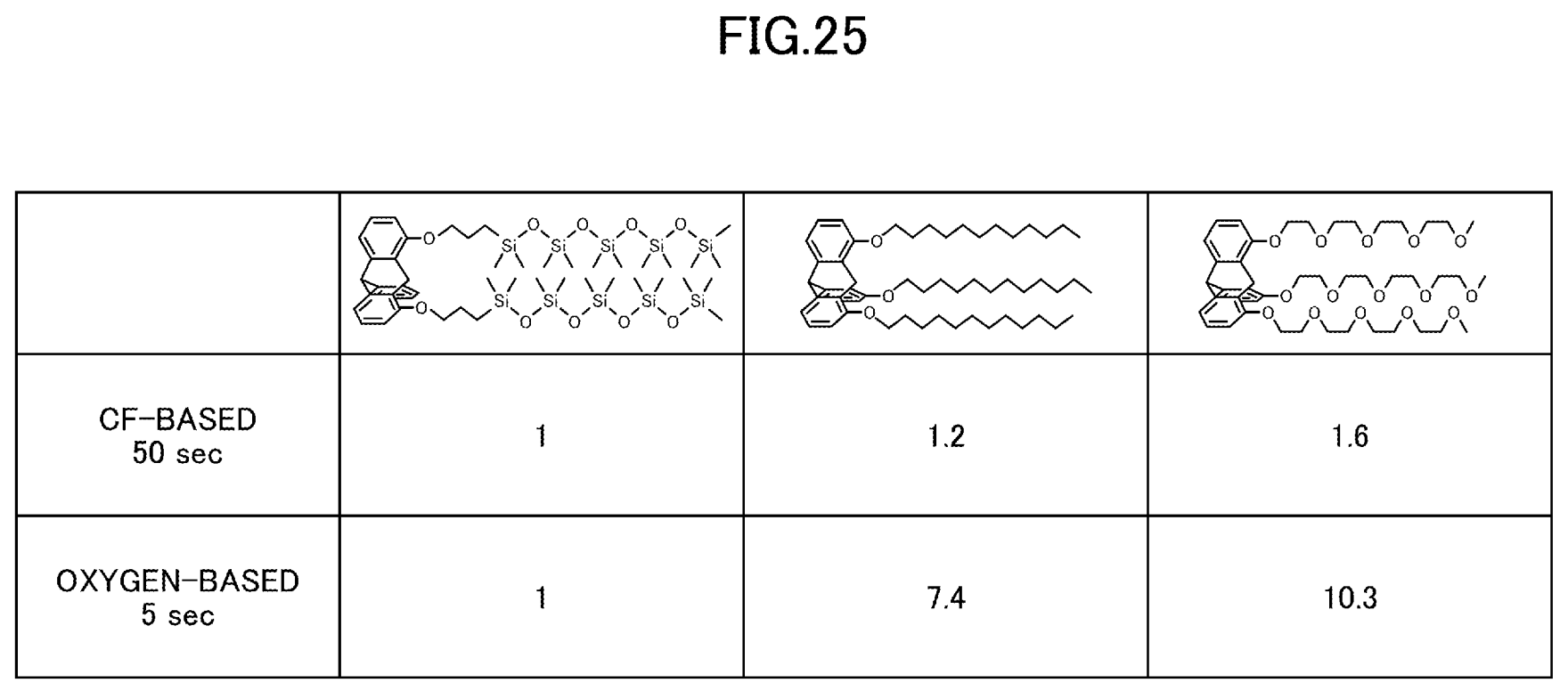

FIG. 23 illustrates an etching amount when a CF (fluorocarbon)-based etching is performed through the process as illustrated in FIG. 22. In the CF-based etching, 50 seconds after the beginning of etching, the side chains are more readily etched in the order of the DMS chain, the TEG chain, and the alkyl (C12) chain (FIG. 25).

Figure 24:
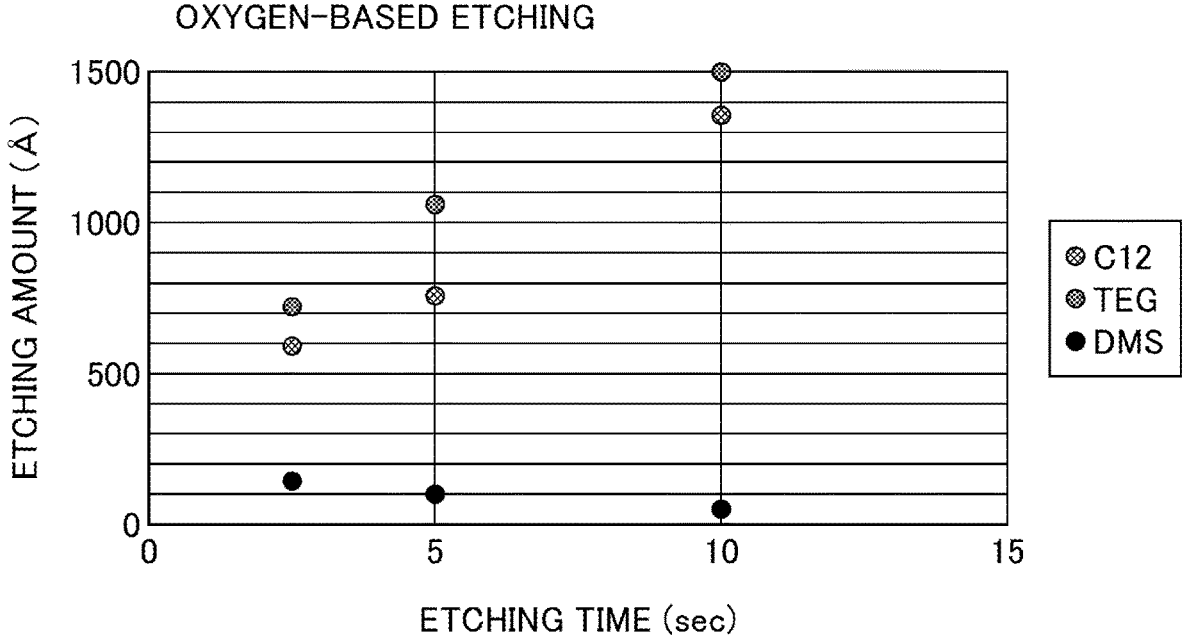
FIG. 24 is a view illustrating a relationship between an etching time and an etching amount for the side chains of the triptycene derivative when an oxygen-based etching is performed in FIG. 22.

FIG. 24 illustrates an etching amount when an oxygen-based etching is performed through the process as illustrated in FIG. 22. In the oxygen-based etching, 5 seconds after the beginning of etching, the side chains are more readily etched in the order of the TEG chain, the alkyl (C12) chain, and the DMS chain (FIG. 25). Note that, compared to the CF-based etching, the difference in etching resistance in the oxygen-based etching is more significant in a short period of time.

Figure 26:
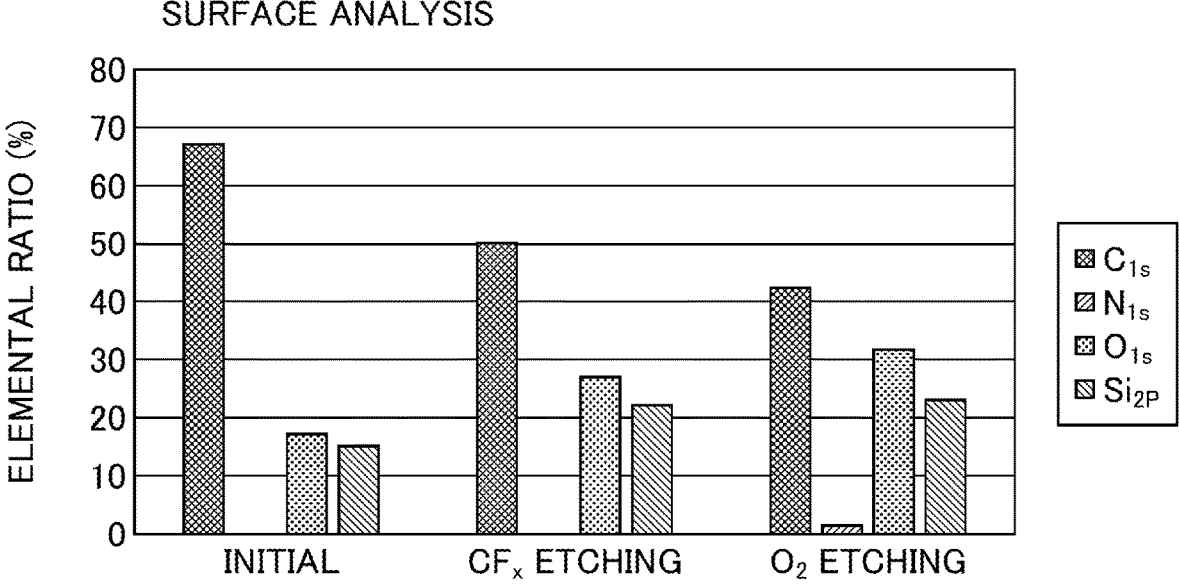
FIG. 26 is a graph illustrating results of elemental analysis after etching in a film surface formed of the triptycene derivative.
Figure 27:
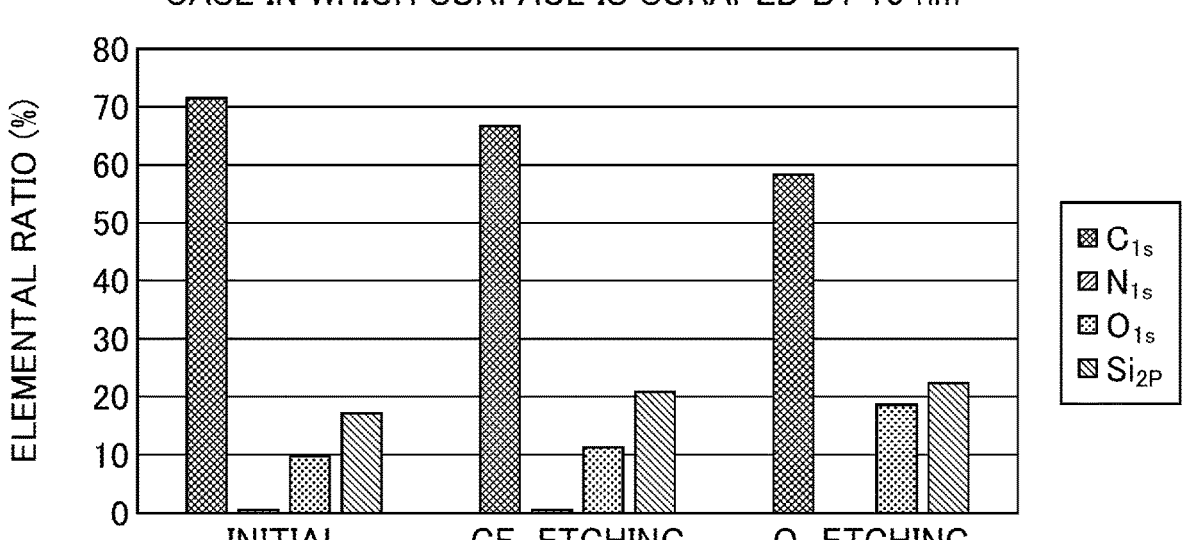
FIG. 27 is a graph illustrating results of elemental analysis when the film surface formed of the triptycene derivative is scraped by 10 nm through argon ion etching.
Figure 28:
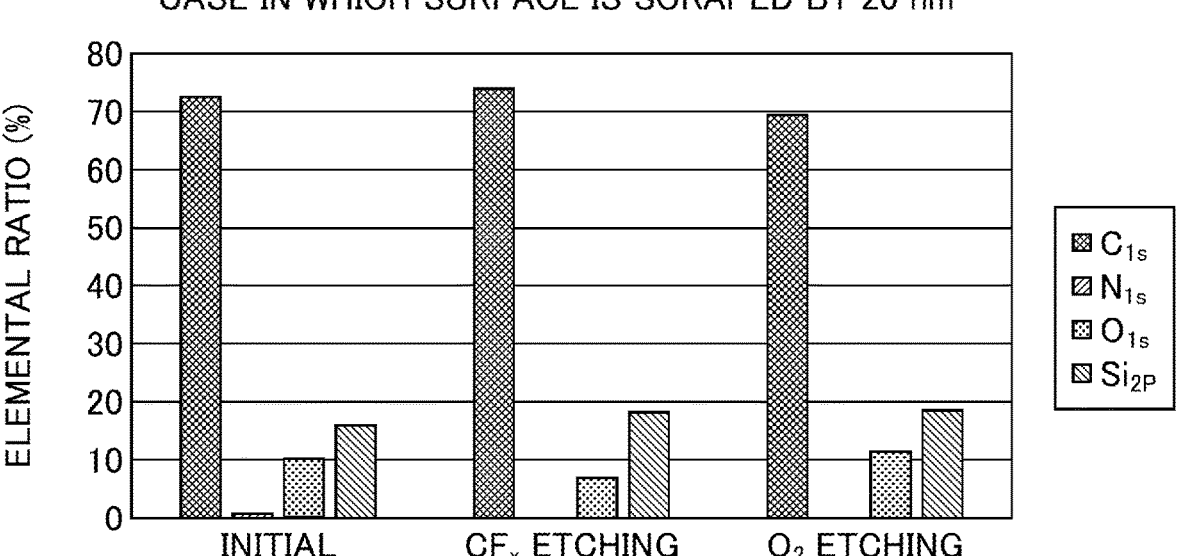
FIG. 28 is a graph illustrating results of elemental analysis when the film surface formed of the triptycene derivative is scraped by 20 nm through argon ion etching.

FIG. 26 is a graph illustrating results of elemental analysis after etching in the film surface formed of the triptycene derivative. FIG. 27 is a graph illustrating results of elemental analysis when the film surface formed of the triptycene derivative is scraped by 10 nm through argon ion etching. FIG. 28 is a graph illustrating results of elemental analysis when the film surface formed of the triptycene derivative is scraped by 20 nm through argon ion etching.

As illustrated in FIG. 26, in the etched surface, the content percentage of carbon is reduced in both of the CF-based etching and the oxygen-based etching. Also, as illustrated in FIG. 27 and FIG. 28, when the surface is scraped by 10 nm or 20 nm, the elemental ratio is returned to the initial state. This indicates that the assembly of the alkyl chains has lower etching resistance, and the assembly of the TEG chains or the DMS chains has etching resistance higher than the etching resistance of the assembly of the alkyl chains.

The plasma processing system of the present embodiment can perform the pattern formation of the present disclosure.

Also, in the present embodiment, by appropriately combining the alkyl chain and the TEG chain or the DMS chain as the side chains, it is possible to apply the first side chain and the second side chain having different etching selectivity ratios as the side chains of the triptycene skeleton.

Figure 29:
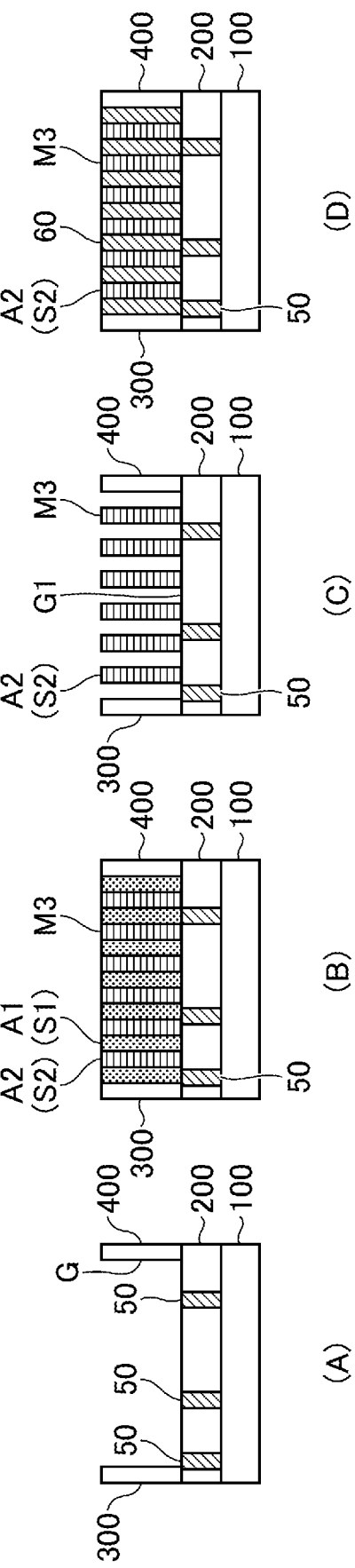
FIG. 29 is a view illustrating steps of forming an interconnecting pattern using the triptycene derivative.
Figure 30:
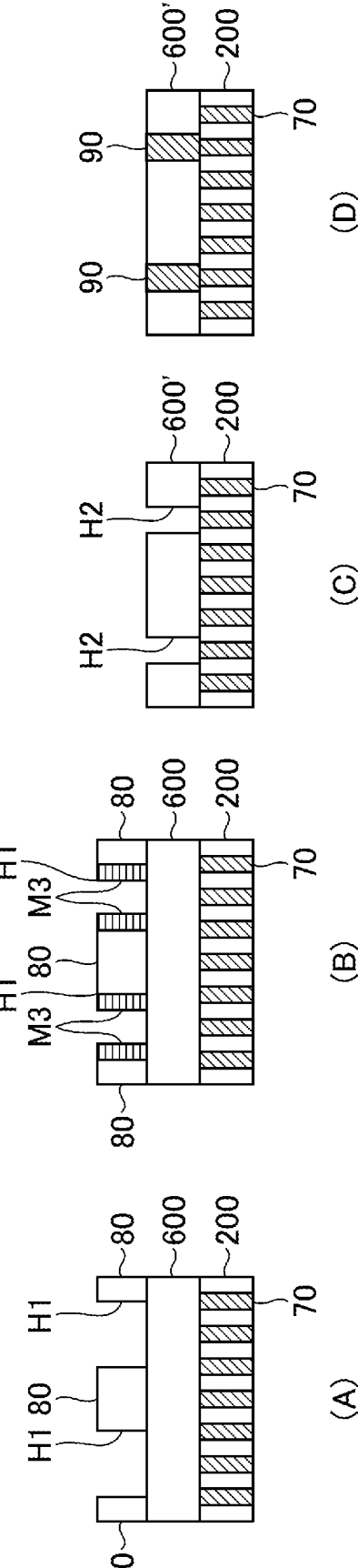
FIG. 30 is a view illustrating steps of forming an interconnecting mask pattern using the triptycene derivative.

The pattern forming method of the present disclosure utilizes the above-described configurations and effects, and thus can also be used for other applications. FIG. 29 is a view illustrating steps of forming an interconnecting pattern using the triptycene derivative. FIG. 30 is a view illustrating steps of forming an interconnecting mask pattern using the triptycene derivative. Note that, in FIG. 29 and FIG. 30, parts common to those in the resist pattern forming steps of FIG. 13 are designated by the corresponding symbols, and description thereof may be omitted.

In the interconnecting pattern forming steps as illustrated in FIG. 29, first, in (A) of FIG. 29, a stack including the substrate 100, the insulating layer 200 thereon, a metal interconnect 50 disposed in the insulating layer 200, and the lateral walls 300 and 400 forming the etching stop layer, is provided.

Gas including the triptycene derivative is supplied to the space G inward of the lateral walls 300 and 400, and a film forming treatment such as vapor deposition, CVD, or the like is performed. Then, as illustrated in (B) of FIG. 29, the molecular assembly layer M3 of the triptycene derivative (the assembly A1 of the first side chains S1 and the assembly A2 of the second side chains S2) is formed in the inner region of the lateral walls 300 and 400.

In (C) of FIG. 29, by performing an etching treatment such as a plasma etching or the like to the molecular assembly layer M3 of the triptycene derivative formed in the inner region of the lateral walls 300 and 400, the assembly A1 of the first side chains S1 is etched and the assembly A2 of the second side chains S2 having etching resistance remains. The space G1 is formed between the assemblies A2 of the second side chains S2.

In (D) of FIG. 29, a metal interconnect 60 is disposed in the space G1 formed between the assemblies A2 of the second side chains S2. The obtained pattern forms an interconnecting pattern in which a part of the metal interconnect 60 is connected to the metal interconnect 50. In this example, the assembly A2 of the second side chains S2 in the molecular assembly layer M3 of the triptycene derivative can function as a part of the interconnecting pattern.

Also, in the interconnecting mask pattern (via mask) forming steps as illustrated in FIG. 30, first, in (A) of FIG. 30, a stack including the insulating layer 200, a metal interconnect 70 disposed in the insulating layer 200, an insulating layer 600 stacked on the insulating layer 200, and a protective layer 80 having a hole H1, is provided.

Gas including the triptycene derivative is supplied into the hole H1 of the protective layer 80, and a film forming treatment such as vapor deposition, CVD, or the like is performed. Then, the layer M3 of the triptycene derivative is formed in the hole H1 of the protective layer 80. In this example, the assembly A1 of the first side chains S1 is disposed inward of the layer M3 of the triptycene derivative, and the assembly A2 of the second side chains S2 is disposed outward thereof.

Then, by performing an etching treatment such as a plasma etching or the like to the molecular assembly layer M3 of the triptycene derivative formed in the hole H1, the assembly A1 of the first side chains S1 is etched and the assembly A2 of the second side chains S2 having etching resistance remains, as illustrated in (B) of FIG. 30. The assembly A2 of the second side chains S2 is formed in an inner wall of the hole H1 of the protective layer 80.

In (C) of FIG. 30, through an etching treatment such as a plasma treatment or the like, an insulating layer 600' having a hole H2 in the insulating layer 600 is formed while the assembly A2 of the second side chains S2 protects the inner wall of the hole H1 of the protective layer 80. After formation of the insulating layer 600', the protective layer 80 is removed together with the assembly A2 of the second side chains S2.

In (D) of FIG. 30, a metal interconnect 90 is buried in the hole H2 of the insulating layer 600', and is conducted to a part of the metal interconnect 70. In the obtained pattern, the metal interconnect 90 forms a via. In this example, the assembly A2 of the second side chains S2 in the molecular assembly layer M3 of the triptycene derivative can function as a via mask.

Figure 31:
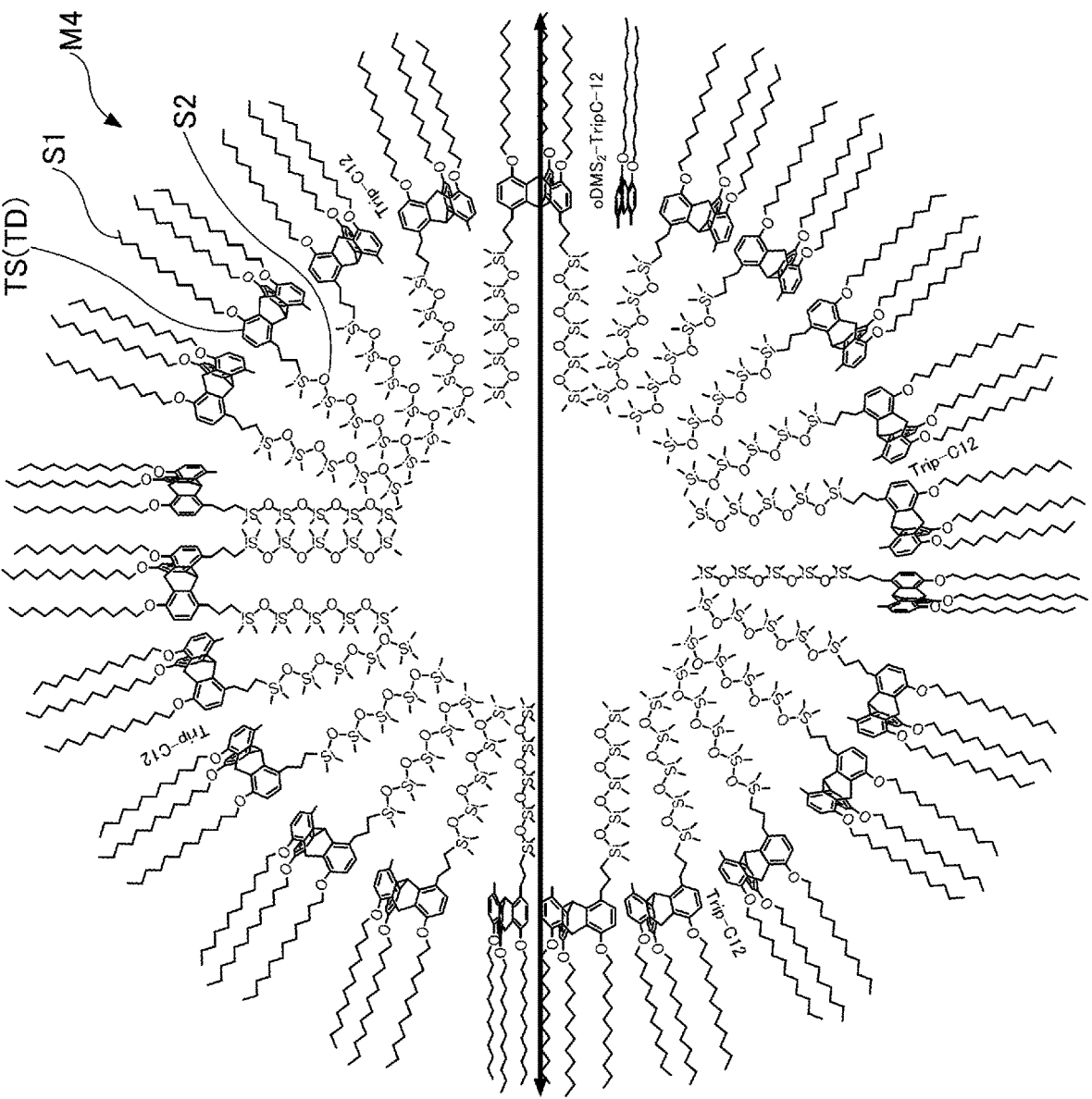
FIG. 31 is a view illustrating a spherical assembly structure of the triptycene derivative.

In the pattern forming method of the present disclosure, moreover, it is possible to control the stacking direction of the lamellar structure so as to be a circumferential direction of a circle in the molecular assembly layer of the triptycene derivative. For example, as illustrated in FIG. 31, it is possible to obtain a molecular assembly layer M4 of the triptycene derivative in which the assembly A1 of the first side chains S1 that are alkyl chains is disposed outward of the circumferential direction, and the assembly A2 of the second side chains S2 that are DMS chains is disposed inward of the circumferential direction.

The molecular assembly layer M4 of the triptycene derivative as described above can form a pattern film in which the assembly A1 of the first side chains S1 and the assembly A2 of the second side chains S2 are stacked in the form of a cylinder in a radial direction. The molecular assembly layer M4 of the triptycene derivative having such a shape can be used for applications of forming the above via mask as illustrated in FIG. 30, or the cylindrical interconnecting pattern.

For example, the embodiments disclosed above include the following embodiments.

(Clause 1)

A pattern forming method, including:

forming a pattern film on a substrate, wherein the pattern film includes a triptycene derivative having a triptycene skeleton, the triptycene skeleton includes a first plane in which position 1, position 8, and position 13 of the triptycene skeleton are arranged, and a second plane in which position 4, position 5, and position 16 of the triptycene skeleton are arranged, and the triptycene derivative includes a first side chain on a one plane side, the one plane side being on a side of one plane from among the first plane and the second plane, and a second side chain on another plane side or on the one plane side, the another plane side being on a side of another plane from among the first plane and the second plane, and the second side chain is different from the first side chain in an etching selectivity ratio.

(Clause 2)

The pattern forming method as described in clause 1, wherein the first side chain is bonded to the triptycene skeleton, and the second side chain is bonded to an end of the first side chain.

(Clause 3)

The pattern forming method as described in clause 1, wherein the first side chain is bonded to the triptycene skeleton at the one plane, and the second side chain is bonded to the triptycene skeleton at the another plane.

(Clause 4)

The pattern forming method as described in any one of clauses 1 to 3, wherein the pattern film is formed in an inner region of two lateral walls that face each other.

(Clause 5)

The pattern forming method as described in clause 4, wherein an aspect ratio of the inner region of the lateral walls is 2 or more.

(Clause 6)

The pattern forming method as described in any one of clauses 1 to 5, wherein the first side chain or the second side chain has an inorganic composition.

(Clause 7)

The pattern forming method as described in clause 6, wherein the inorganic composition includes a siloxane compound.

(Clause 8)

The pattern forming method as described in any one of clauses 1 to 7, wherein the first side chain or the second side chain has an organic composition.

(Clause 9)

The pattern forming method as described in clause 8, wherein an end of the first side chain or the second side chain having the organic composition is hydroxy-terminated.

(Clause 10)

A plasma processing method, including:

etching the pattern film formed by the pattern forming method as described in any one of clauses 1 to 9, with a plasma treatment.

While embodiments of the present disclosure have been described above, the present disclosure is not limited to the above-described embodiments, and various alterations and modifications are possible within the disclosed scope of claims as recited.

The present application claims priority to Japanese Patent Application No. 2021-114353, filed Jul. 9, 2021, the contents of which are incorporated herein by reference in their entirety.

REFERENCE SIGNS LIST

TS triptycene (triptycene skeleton)

TD single molecule of triptycene derivative

M1 assembly structure of molecules forming existing pattern film

M2 two-dimensional assembly structure of triptycene

M3 three-dimensional assembly structure of triptycene

S1 first side chain

S2 second side chain

A1 assembly of first side chains

A2 assembly of second side chains 40 exhausting system 100 substrate 200,200' insulating layer 300,400 lateral wall G,G1,G2 space 1 plasma processing device 10 plasma processing chamber 10a lateral wall 10e gas exhausting port 10s chamber space 11 substrate support 111 body 111a center region (substrate support surface)

111b annular region (ring support surface)

112 ring assembly

W wafer 13 shower head 13a gas supplying port 13b gas diffusing chamber 13c gas introducing port 2 controller 2a computer 2a1 processor 2a2 storage 2a3 communication interface 20 gas supply 21 gas source 22 flow rate controller 30 power supply 31 RF power supply 31a first RF generator 31b second RF generator 32 DC power supply 32a first DC generator 32b second DC generator 5 substrate 6,600 insulating layer 7,7',8,8',80 protective layer 9,9' pattern film 50,60,70,90 metal interconnect H1,H2 hole.

The invention claimed is:

1. A pattern forming method, comprising:

forming a molecular assembly layer of a triptycene derivative having a triptycene skeleton on a substrate, wherein the molecular assembly layer of the triptycene derivative has an assembly structure in which a plurality of single molecules of the triptycene derivative are aligned and assembled in a horizonal direction and a vertical direction, the assembly structure including a first assembly being a vertical stack of first side chains of the triptycene derivative and a second assembly being a vertical stack of second side chains of the triptycene derivative, that are alternatingly arranged in the horizontal direction; and performing an etching treatment to the molecular assembly layer of the triptycene derivative such that the first assembly is etched and the second assembly remains, thereby forming a pattern on the substrate, wherein the triptycene skeleton includes a first plane in which position 1, position 8, and position 13 of the triptycene skeleton are arranged, and a second plane in which position 4, position 5, and position 16 of the triptycene skeleton are arranged, and the triptycene derivative includes the first side chain on a one plane side, the one plane side being on a side of one plane from among the first plane and the second plane, and the second side chain on another plane side or on the one plane side, the another plane side being on a side of another plane from among the first plane and the second plane, and the second side chain is different from the first side chain in an etching selectivity ratio.

2. The pattern forming method according to claim 1, wherein the first side chain is bonded to the triptycene skeleton, and the second side chain is bonded to an end of the first side chain.

3. A plasma processing method, comprising:

etching the molecular assembly layer formed by the pattern forming method according to claim 2, with a plasma treatment.

4. The pattern forming method according to claim 1, wherein the first side chain is bonded to the triptycene skeleton at the one plane, and the second side chain is bonded to the triptycene skeleton at the another plane.

5. A plasma processing method, comprising:

etching the molecular assembly layer formed by the pattern forming method according to claim 4, with a plasma treatment.

6. The pattern forming method according to claim 1, wherein the molecular assembly layer is formed in an inner region of two lateral walls that face each other.

7. The pattern forming method according to claim 6, wherein an aspect ratio of the inner region of the lateral walls is 2 or more.

8. A plasma processing method, comprising:

etching the molecular assembly layer formed by the pattern forming method according to claim 7, with a plasma treatment.

9. A plasma processing method, comprising:

etching the molecular assembly layer formed by the pattern forming method according to claim 6, with a plasma treatment.

10. The pattern forming method according to claim 1, wherein the first side chain or the second side chain has an inorganic composition.

11. The pattern forming method according to claim 10, wherein the inorganic composition includes a siloxane compound.

12. A plasma processing method, comprising:

etching the molecular assembly layer formed by the pattern forming method according to claim 11, with a plasma treatment.

13. A plasma processing method, comprising:

etching the molecular assembly layer formed by the pattern forming method according to claim 10, with a plasma treatment.

14. The pattern forming method according to claim 1, wherein the first side chain or the second side chain has an organic composition.

15. The pattern forming method according to claim 14, wherein an end of the first side chain or the second side chain having the organic composition is hydroxy-terminated.

16. A plasma processing method, comprising:

etching the molecular assembly layer formed by the pattern forming method according to claim 15, with a plasma treatment.

17. A plasma processing method, comprising:

etching the molecular assembly layer formed by the pattern forming method according to claim 14, with a plasma treatment.

18. A plasma processing method, comprising:

etching the molecular assembly layer formed by the pattern forming method according to claim 1, with a plasma treatment.

* * * * *